United States Patent
Hoover et al.

(10) Patent No.: US 10,359,434 B2
(45) Date of Patent: Jul. 23, 2019

(54) IN VITRO DETECTION OF PRIONS IN BLOOD

(71) Applicants: Edward A. Hoover, Loveland, CO (US); Candace K. Mathiason, Windsor, CO (US)

(72) Inventors: Edward A. Hoover, Loveland, CO (US); Candace K. Mathiason, Windsor, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 47 days.

(21) Appl. No.: 15/330,832

(22) Filed: Nov. 7, 2016

(65) Prior Publication Data

US 2017/0059585 A1    Mar. 2, 2017

Related U.S. Application Data

(63) Continuation-in-part of application No. 14/920,422, filed on Oct. 22, 2015, now abandoned.

(60) Provisional application No. 62/067,016, filed on Oct. 22, 2014.

(51) Int. Cl.
    *G01N 33/68*    (2006.01)
(52) U.S. Cl.
    CPC ..... *G01N 33/6893* (2013.01); *G01N 33/6896* (2013.01); *G01N 2800/2828* (2013.01)
(58) Field of Classification Search
    CPC ........... G01N 33/6896; G01N 33/6893; G01N 2333/4709; G01N 2800/28; G01N 2800/2821
    See application file for complete search history.

(56) References Cited

U.S. PATENT DOCUMENTS 7,351,526 B2    4/2008    Soto et al.
2011/0311997 A1    12/2011    Soto et al.

OTHER PUBLICATIONS

Elder et al. PLoS One. Nov. 1, 2013;8(11):e80203. doi: 10.1371/journal.pone.0080203. eCollection 2013.*
Smith et al. Fate of Prions in Soil: A Review. J Environ Qual. Mar.-Apr. 2011; 40(2): 449-461.*
Properzi et al. Physical, chemical and kinetic factors affecting prion infectivity. Prion. May-Jun. 2016; 10(3): 251-261.*
Mathiason et al., Infectious Prions in the Saliva and Blood of Deer with Chronic Wasting Disease. Science. 2006. vol. 314: 133-136.
Murayama et al., Urinary excretion and blood level of prions in scrapie-infected hamsters. J Gen Viral. 2007. vol. 88: 2890-2898.
Houston et al., Prion diseases are efficiently transmitted by blood transfusion in sheep. Blood. 2008. vol. 112 (No. 12): 4739-4745.
Orru et al., Human variant Creutzfeldt-Jakob disease and sheep scrapie PrP(res) detection using seeded conversion of recombinant prion protein. Protein Eng Des Sel. 2009. vol. 22 (No. 8): 515-521.
Castilla et al., In Vitro Generation of Infectious Scrapie Prions. Cell. 2005. vol. 121: 195-206.
Terry et al., Detection of PrPsc in blood from sheep infected with the scrapie and bovine spongiform encephalopathy agents. J Virol. 2009. vol. 83 (No. 23): 12552-12558.
D'Castro et al., Isolation of Proteinase K-Sensitive Prions Using Pronase E and Phosphotungstic Acid. PLoS One. 2010. vol. 5 (No. 12): e15679.
McCutcheon et al., All Clinically-Relevant Blood Components Transmit Prion Disease following a Single Blood Transfusion: A Sheep Model of vCJD. PLoS One. 2011. vol. 6 (No. 8): e23169.
Bannach et al., Detection of prion protein particles in blood plasma of scrapie infected sheep. PLoS One. 2012. vol. 7 (No. 5): e36620.
Lacroux et al., Impact of leucocyte depletion and prion reduction filters on TSE blood borne transmission. PLoS One. 2012. vol. 7 (No. 7): e42019.
Wilham et al., Rapid end-point quantitation of prion seeding activity with sensitivity comparable to bioassays. PLoS Pathog. 2010. vol. 6 (No. 12): e1001217.
Orrú et al., Prion Disease Blood Test Using Immunoprecipitation and Improved Quaking-Induced Conversion. MBio. 2011. vol. 2 (Issue 3): e00078-11.
Orru et al., New generation QuIC assays for prion seeding activity. Prion. 2012. vol. 6 (No. 2): 147-152.
Gonzalez-Romero et al., Detection of infectious prions in urine. FEBS Lett. 2008. vol. 582 (Nos. 21-22): 3161-3166.
Morales et al., Reduction of prion infectivity in packed red blood cells. Biochem Biophys Res Commun. 2008. vol. 377 (No. 2): 373-378.
Chen et al., Estimating prion concentration in fluids and tissues by quantitative PMCA. Nature Methods. 2010. vol. 7 (No. 7): 519-520.
Barria et al., Cyclic amplification of prion protein misfolding. Methods Mol Biol. 2012. vol. 849: 199-212.
Wroe et al., Clinical presentation and pre-mortem diagnosis of variant Creutzfeldt-Jakob disease associated with blood transfusion: a case report. The Lancet. 2006. vol. 368: 2061-2067.

(Continued)

*Primary Examiner* — Gregory S Emch
(74) *Attorney, Agent, or Firm* — Michael M. McGaw; Smith & Hopen, P.A.

(57) ABSTRACT

A method of screening a blood sample for the presence of prions. The method includes the steps of collecting the blood sample in heparin, contacting the sample with a solution comprising recombinant prion protein (rPrP) and Thioflavin T (ThT), and measuring the resulting ThT fluorescence in the sample. The method can further include the step of freezing and thawing the sample prior to contacting the sample with a solution comprising recombinant prion protein (rPrP) and Thioflavin T (ThT). The method can also include the step of precipitating the prions in sodium phosphotungstic acid (NaPTA) prior to contacting the sample with a solution comprising recombinant prion protein (rPrP) and Thioflavin T (ThT).

18 Claims, 25 Drawing Sheets

(56) References Cited

OTHER PUBLICATIONS

Edgeworth et al., Detection of prion infection in variant Creutzfeldt-Jakob disease: a blood-based assay. The Lancet. 2011. vol. 377: 487-493.
Group, U.B.S.P.W. Creutzfeldt-Jakob Disease: Joint UKBTS / HPA Professional Advisory Committee Position Statement. 2015. http://www.transfusionguidelines.org/document-library/documents/jpac-position-statement-vcjd-may-2015/download-file/Position%20Statement%20on%20vCJD%20May%202015.pdf.
Andreoletti et al., Highly efficient prion transmission by blood transfusion. PLoS Pathog. 2012. vol. 8 (No. 6): e1002782.
Soto et al., Pre-symptomatic detection of prions by cyclic amplification of protein misfolding. FEBS Letters. 2005. vol. 579: 638-642.
Saa et al., Presymptomatic detection of prions in blood. Science. 2006. vol. 313: 92-94.
Atarashi et al., Ultrasensitive detection of scrapie prion protein using seeded conversion of recombinant prion protein. Nat Methods. 2007. vol. 4 (No. 8): 645-650.
Castilla et al., Detection of prions in blood. Nat Med. 2005. vol. 11 (No. 9): 982-985.
Glier and Holada, Blood storage affects the detection of cellular prion protein on peripheral blood leukocytes and circulating dendritic cells in part by promoting platelet satellitism. J Immunol Methods. 2012. vol. 380: 65-72.
Saa et al., Cyclic amplification of protein misfolding and aggregation. Methods Mol Biol. 2005. vol. 299: 53-65.
Yokoyama et al., Heparin enhances the cell-protein misfolding cyclic amplification efficiency of variant Creutzfeldt-Jakob disease. Neurosci Lett. 2011. 498: 119-123.

\* cited by examiner

IN VITRO DETECTION OF PRIONS IN BLOOD

CROSS-REFERENCE TO RELATED APPLICATIONS

This application is a continuation-in-part of U.S. application Ser. No. 14/920,422, filed Oct. 22, 2015, which claims the benefit of U.S. Provisional Application No. 62/067,016, filed Oct. 22, 2014.

STATEMENT OF GOVERNMENT INTEREST

This invention was made with government support under Grant Nos. R01 NS061902, N01 AI025491 and R01 AI093634 awarded by the National Institutes of Health. The government has certain rights in the invention.

FIELD OF INVENTION

This invention relates to infectious agent screening and diagnoses. More specifically, this invention relates to in vitro detection of prions and infectious proteins in blood.

BACKGROUND OF THE INVENTION

The hematogenous spread of prions in transmissible spongiform encephalopathy (TSE)-infected animals has long been hypothesized, but evidence for the presence of prions in non-nervous/lymphoid tissues and blood was not available for several decades. Later studies have provided unequivocal proof of efficient TSE blood-borne infectivity [Andreoletti, O., et al., PLoS Pathog, 2012. 8(6): p. e1002782]. The knowledge that prions traffic throughout the body in blood has important implications for both human and animal health.

Variant Creutzfeldt-Jakob disease (vCJD) emerged following the bovine spongiform encephalopathy (BSE) epidemic in the United Kingdom in the 1980s and 90s. Biochemical and strain typing analysis have provided evidence indicating that vCJD originated from human exposure to BSE contaminated material. To date, 225 cases of vCJD have been diagnosed worldwide, four of which have been transmitted by non-leucodepleted blood transfusion [Team, E., Euro Surveill, 2007. 12(1): p. E070118 4; Wroe, S. J., et al., The Lancet, 2006. 368(9552): p. 2061-2067]. While leucocyte reduction has been implemented to filter prions and prion carrying cells from blood products, current filtration methodologies are unable to remove 100% of TSE infectivity [Lacroux, C., et al., PLoS One, 2012. 7(7): p. e42019.]. In addition, recent reports have revealed that $\frac{1}{1,250}$ to $\frac{1}{3,500}$ persons in the United Kingdom may be asymptomatic carriers of vCJD as a result of the BSE epidemic. Thus, concern exists that a secondary outbreak of vCJD may ensue involving blood-borne prion transmission originating from individuals unknowingly carrying a subclinical prion infection [McCutcheon, S., et al., PLOS ONE, 2011. 6(8): p. e23169.] The present invention addresses the need for an in vitro assay with the ability to detect the prion disease-associated isoform of prion protein ($PrP^D$) present in whole blood.

Several animal TSEs, including chronic wasting disease (CWD) of deer and elk and hamster-adapted transmissible spongiform encephalopathy (TME) exhibit a hematogenous phase of infection, thus providing excellent TSE models for the development of an ante-mortem blood-borne $PrP^D$ detection assay.

While traditional assays, such as Western blot and immunohistochemistry (IHC), are effective for detecting large quantities of prions present in nervous and lymphoid tissue, they do not have the ability to detect the minute quantities thought to be present in bodily fluids or peripheral tissues early in infection. Rodent bioassays have the necessary sensitivity and specificity to detect hematogenous prions, but they are not realistic as rapid and cost-effective diagnostic tools. In vitro prion detection was advanced with the advent of serial protein misfolding cyclic amplification (sPMCA) [Saa, P. et al., Science, 2006. 313(5783): p. 92-4; Saa, P., et al., Methods Mol Biol, 2005. 299: p. 53-65.]. sPMCA requires less time than bioassay [Castilla, J., et al., Nat Med, 2005. 11(9): p. 982-5.], but has been hampered by a lack of consistent sensitivity and a dependence on protease digestion prior to immunoassay readout. In contrast, the real-time quaking-induced conversion (RT-QuIC) assay [Atarashi, R., et al., Nat Methods, 2007. 4(8): p. 645-50; Orrú, C. D., et al., mBio, 2011. 2(3): p. e00078-11; Wilham, J. M., et al., PLoS Pathog, 2010. 6(12): p. e1001217.] relies upon the seeded conversion of recombinant prion protein (rPrP) to $PrP^D$ and subsequent binding of thioflavin T (ThT) to the resulting amyloid isoforms [Krebs, M. R., et al., J Struct Biol, 2005. 149(1): p. 30-7.], thus offering enhanced antemortem prion detection and real-time fluorescence readout. However, improvement in the sensitivity and specificity of RT-QuIC would be very desirable.

The present invention provides new techniques and methodologies to improve the sensitivity and specificity of prior amplification and detection techniques, such as RT-QuIC, while maintaining fast, sensitive and consistent assays for the detection of blood-borne prions.

SUMMARY OF THE INVENTION

The present invention provides extremely sensitive methods for detecting prion protein, including $PrP^{res}$ or $PrP^{Sc}$, in a sample The modified $rPrP^D$ amplification assays are surprisingly much faster than existing PMCA methods, yet it still retains sufficient sensitivity to detect extremely low levels of $PrP^D$. The method permits the rapid identification and diagnosis of prion disease, which can limit the transmission of prion diseases, particularly through the blood supply.

Blood-borne transmission of infectious prions during the asymptomatic or pre-clinical stage of disease occurs for both human and animal transmissible spongiform encephalopathies (TSEs). The geographical distribution of the cervid TSE, chronic wasting disease (CWD), continues to spread across North America and the prospective number of individuals harboring an asymptomatic infection of human variant Creutzfeldt-Jakob Disease (vCJD) in the United Kingdom has been projected to be ~1 in 3000 residents. Thus, it is important to monitor cervid and human blood products to ensure herd health and human safety. Current methods for detecting blood-associated prions rely primarily upon bioassay in laboratory animals. While bioassay provides high sensitivity and specificity, it requires many months, animals, and costs. Modifications of the real time quaking-induced conversion (RT-QuIC) assay enables detection of blood-borne prions in whole blood from prion-infected preclinical white-tailed deer, muntjac deer, and Syrian hamsters, attaining sensitivity of >90% while maintaining 100% specificity. Our results indicate that RT-QuIC methodology as modified and taught herein can provide consistent and reliable detection of blood-borne prions in pre-clinical and symptomatic stages of two animal TSEs, offering promise for prionemia detection in other species, including humans.

The long-standing but heretofore unfulfilled need for is now met by a new, useful, and nonobvious invention. In a first aspect the present invention provides a method for the amplification of a prion disease-associated conformer of prion protein ($PrP^D$; also sometimes referred to as $PrP^{res}$ or $PrP^{Sc}$) in a blood sample. The method includes the steps of providing a blood sample (such as from a human, cervid or domesticated animal) containing a $PrP^D$ (or to be tested for the presence of $PrP^D$); contacting the blood sample with heparin (such as through the addition of heparin to the sample or by collecting the sample in a heparinized tube); freezing the heparinized blood sample; thawing the heparinized blood sample; contacting the heparinized blood sample with an excess of a non-pathogenic conformer of $PrP^C$ or a non-pathogenic conformer of recombinant PrP; incubating the heparinized blood sample with the non-pathogenic conformer; disaggregating any aggregates of $PrP^D$ formed during the incubating step; and repeating the incubating and disaggregating steps one or more times to yield an amplified $PrP^D$ in the sample.

Disaggregation can be performed via techniques designed to physically disrupt the aggregates, such as sonication or by shaking the incubation mixtures.

Repeating the incubating and disaggregating steps allows for the exponential (geometric) increase of the $PrP^D$ in the sample in a manner similar to that achieved with PCR. An excess of a non-pathogenic conformer of $PrP^C$ or a non-pathogenic conformer of recombinant PrP is used in the incubation mix to ensure that the supply of substrate is not exhausted given the number of rounds of the incubating and disaggregating steps. Often this technique will be employed for the detection of $PrP^D$ in a sample, such as a blood sample. The general goal is to take an undetectable amount of $PrP^D$ in the sample as collected and amplify that $PrP^D$ to detectable levels. Accordingly, there needs to be a sufficient $PrP^C$ or a non-pathogenic conformer of recombinant PrP in the reaction mix, and a sufficient number of incubating and disaggregating cycles, to bring the $PrP^D$ up to detectable levels.

In certain embodiments the sample can be frozen at a temperature of about 0° C. or colder, about −10° C. or colder, about −20° C. or colder, about −40° C. or colder, about −60° C. or colder, or about −80° C. or colder. In a preferred embodiment the samples are frozen at about −80° C. or colder. In certain embodiments the sample is frozen for about 2 minutes or more, about 5 minutes or more, about 10 minutes or more, about 15 minutes or more, about 20 minutes or more, about 30 minutes or more, about 45 minutes or more, or about 60 minutes or more. In a preferred embodiment the samples are frozen for about 30 minutes.

In certain embodiments the sample can be thawed at a temperature of 0° C. or warmer, about 4° C. or warmer, about 10° C. or warmer, about 15° C. or warmer, about 20° C. or warmer, or about 22° C. or warmer. In a preferred embodiment the samples are thawed at about 22° C. or warmer. In certain embodiments the sample is thawed for about 2 minutes or more, about 5 minutes or more, about 10 minutes or more, about 15 minutes or more, about 20 minutes or more, about 30 minutes or more, about 45 minutes or more, or about 60 minutes or more. In a preferred embodiment the samples are thawed for about 60 minutes.

It is contemplated that the techniques of the invention can be applied to various prion amplification and detection methods, including QuIC, S-QuIC, RT-QuIC, eQuIC, PMCA, sPMCA, and rPrP-PMCA.

The freezing and thawing steps can be performed a plurality of times (e.g. two times, three times or four or more times) before the incubating step of the first aspect. In a preferred embodiment the steps of freezing and thawing are performed four times.

In certain embodiments the method of the first aspect can include the step of precipitating the $PrP^D$ in a blood sample sodium phosphotungstic acid (NaPTA) following the thawing step and prior to amplifying the $PrP^D$. The precipitation step is thought to remove components in the sample that interfere with the amplification of $PrP^D$.

In an advantageous embodiment the method can include the step of screening the amplified $PrP^D$ for the presence of $PrP^D$. In other words, it will often be unknown whether a particular sample contains $PrP^D$. By virtue of the amplification, the $PrP^D$ in the sample, if any, should have been increased to detectable levels, where it would not have been detectable prior to amplification. The absence of $PrP^D$ in the sample upon attempted detection after amplification would indicate that the original sample was free of $PrP^D$. In a similar manner, the method can include the step of contacting the sample with thioflavin T (ThT) prior to an incubating step and measuring the fluorescence of the resulting sample after an incubating step. The fluorescence of the ThT in the sample following incubation allows the presence of $PrP^D$ in the sample to be determined. More particularly, the fluorescence emitted by the sample increases upon the transition of $PrP^C$ to $PrP^D$. Therefore, an increase in the fluorescence will correlate with an increase in the amount of PrPin the sample.

In a second aspect the present invention provides a method for the detection of a prion disease-associated conformer of prion protein ($PrP^D$) in a sample. The method of the second aspect includes the steps of providing a sample to be screened for $PrP^D$; freezing and thawing the sample; contacting the thawed sample with an excess of a non-pathogenic conformer of $PrP^C$ or a non-pathogenic conformer of recombinant PrP; incubating the contacted sample with the non-pathogenic conformer; disaggregating any aggregates of $PrP^D$ formed during the incubating step; repeating the incubating and disaggregating steps one or more times to yield an amplified $PrP^D$ in the sample; and screening the incubated sample for $PrP^D$. The method of the second aspect amplifies the $PrP^D$ in the sample, if any, to detectable levels. In an advantageous embodiment the method can include the steps of contacting the sample with ThT prior to an incubating step and measuring the fluorescence of the resulting sample after an incubating step. The level of fluorescence of the ThT in the sample following incubation allows the presence of $PrP^D$ in the sample to be determined.

In additional embodiments heparin can be added to the sample prior to the incubating step. In a preferred embodiment about 200 units/ml of heparin are added to the sample prior to the incubating step.

In certain embodiments the sample can be frozen at a temperature of about 0° C. or colder, about −10° C. or colder, about −20° C. or colder, about −40° C. or colder, about −60° C. or colder, or about −80° C. or colder. In a preferred embodiment the samples are frozen at about −80° C. or colder. In certain embodiments the sample is frozen for about 2 minutes or more, about 5 minutes or more, about 10 minutes or more, about 15 minutes or more, about 20 minutes or more, about 30 minutes or more, about 45 minutes or more, or about 60 minutes or more. In a preferred embodiment the samples are frozen for about 30 minutes.

In certain embodiments the sample can be thawed at a temperature of 0° C. or warmer, about 4° C. or warmer, about 10° C. or warmer, about 15° C. or warmer, about 20° C. or warmer, or about 22° C. or warmer. In a preferred embodiment the samples are thawed at about 22° C. or warmer. In certain embodiments the sample is thawed for about 2 minutes or more, about 5 minutes or more, about 10 minutes or more, about 15 minutes or more, about 20 minutes or more, about 30 minutes or more, about 45 minutes or more, or about 60 minutes or more. In a preferred embodiment the samples are thawed for about 60 minutes.

The freezing and thawing steps can be performed a plurality of times (e.g. two times, three times or four or more times) before the incubating step of the first aspect. In a preferred embodiment the steps of freezing and thawing are performed four times. The method can further include the step of homogenizing the sample after the freezing and thawing steps.

The method can also include the step of contacting the sample with thioflavin T (ThT) prior to an incubating step and measuring the fluorescence of the resulting sample after an incubating step.

In a third aspect the present invention provides a method for the detection of a prion disease-associated conformer of prion protein ($PrP^D$) in a blood sample. The method of the third aspect includes the steps of comprising the steps of providing a blood sample to be screened for $PrP^D$; freezing the blood sample; thawing the blood sample; contacting the blood sample with an excess of a non-pathogenic conformer of recombinant PrP; incubating the blood sample with the non-pathogenic conformer; disaggregating any aggregates of $PrP^D$ formed during the incubating step; repeating the incubating and disaggregating steps one or more times to yield an amplified $PrP^D$ in the sample; and screening the incubated sample for $PrP^D$, whereby the method amplifies the $PrP^D$ in the sample to detectable levels.

BRIEF DESCRIPTION OF THE DRAWINGS

For a fuller understanding of the invention, reference should be made to the following detailed description, taken in connection with the accompanying drawings, in which:

FIGS. 1A-1C are a series of three graphs showing RT-QuIC analysis of whole blood collected in various anticoagulants. Blood was collected from a CWD-infected and CWD-naïve white-tailed deer and preserved in one of three anticoagulants: CPDA, EDTA or heparin. Serial blood sample dilutions (neat to $10^{-6}$) were assayed by RT-QuIC for 60 hours and ThT fluorescence level above threshold determined positivity. Detection of $PrP^C$ converting activity for each replicate is shown for blood collected in CPDA (FIG. 1A), EDTA (FIG. 1B) and heparin (FIG. 1C).

FIG. 1A is a graph showing the detection of $PrP^C$ converting activity for blood collected in CPDA.

FIG. 1B is a graph showing the detection of $PrP^C$ converting activity for blood collected in EDTA.

FIG. 1C is a graph showing the detection of $PrP^C$ converting activity for blood collected in heparin.

FIGS. 2A and 2B are a pair of graphs showing RT-QuIC analysis of fresh versus frozen whole blood. Blood was collected from a CWD-infected and CWD-naïve white-tailed deer and aliquots were analyzed immediately (fresh) or frozen (−80 C). Serial blood sample dilutions (neat to $10^{-6}$) were assayed by RT-QuIC in duplicate for 60 hours and ThT fluorescence level above threshold determined positivity. Detection of $PrP^C$ converting activity for each replicate is shown for blood analyzed fresh (A) and frozen (B).

FIG. 2A is a graph showing the detection of $PrP^C$ converting activity for blood analyzed fresh.

FIG. 2B is a graph showing the detection of $PrP^C$ converting activity for blood analyzed frozen.

FIGS. 3A-3F are a series of six graphs showing RT-QuIC analysis of samples before and after treatment with NAPTA. Samples were untreated or precipitated using NAPTA, serially diluted (neat to $10^{-6}$), and assayed by RT-QuIC in triplicate for 60 hours. ThT fluorescence level above threshold determined positivity, each replicate is present. (A) Limited detection is seen in untreated blood samples. (B-D) Improved detection of $PrP^C$ converting activity is seen in blood samples precipitated with NAPTA from CWD-infected white-tailed deer (B and C). No $PrP^C$ converting activity was seen in samples precipitated with NAPTA from a CWD-naïve white-tailed deer (D).

FIG. 3A shows the limited detection of $PrP^C$ converting activity in untreated (i.e. Non-NaPTA) frozen blood samples from a first CWD-infected white-tailed deer (Animal #6) by RT-QuIC analysis.

FIG. 3B shows improved detection of $PrP^C$ converting activity in frozen blood samples precipitated with NAPTA from the first CWD-infected white-tailed deer (Animal #6) as tested in FIG. 3A.

FIG. 3C shows the absence of detection of $PrP^C$ converting activity in untreated (i.e. Non-NaPTA) frozen blood samples from a second CWD-infected white-tailed deer (Animal #16) by RT-QuIC analysis.

FIG. 3D shows the detection of $PrP^C$ converting activity in frozen blood samples precipitated with NAPTA from the second CWD-infected white-tailed deer (Animal #16) as tested in FIG. 3C.

FIG. 3E shows the results of detection of $PrP^C$ converting activity in untreated (i.e. Non-NaPTA) frozen blood samples from a naive white-tailed deer (Animal #23) by RT-QuIC analysis.

FIG. 3F shows the absence of detection of $PrP^C$ converting activity in frozen blood samples precipitated with NAPTA from a naive white-tailed deer (Animal #23) as tested in FIG. 3E.

FIG. 4 is a graph showing RT-QuIC comparison of brain and blood samples. Ten percent (10%) brain homogenates were serially diluted ($10^{-5}$ to $10^{-8}$) and assayed by RT-QuIC for 60 hours. Blood samples were diluted to $10^{-2}$ and run in triplicate for 60 hours with ThT fluorescence level above threshold determining positivity. CWD-infected blood diluted $10^{-2}$ is seen to have similar levels of $PrP^C$ converting activity as CWD-positive brain diluted $10^{-6}$ and $10^{-7}$. UN=Uninfected; INF=Infected.

FIGS. 5A-5F are a series of six graphs showing RT-QuIC analysis of cervid whole blood samples. Blood samples were diluted to $10^{-2}$ and 8 replicates were analyzed over 2 runs of 60 hours, and positivity was determined by ThT fluorescence level above threshold. $PrP^C$ converting activity is demonstrated in 22 CWD infected cervid blood samples, and is absent in all CWD-naïve samples (A-F). Each line is the average of four replicates for a specific animal. UN=Uninfected; INF=Infected.

FIG. 5A is a graph showing the first run of RT-QuIC analysis of cervid whole blood samples from the first cervid group.

FIG. 5B is a graph showing the second run of RT-QuIC analysis of cervid whole blood samples from the first cervid group.

FIG. 6A is a graph showing the first run of RT-QuIC analysis of hamster whole blood samples from the first hamster group.

FIG. 6B is a graph showing the second run of RT-QuIC analysis of hamster whole blood samples from the first hamster group.

FIG. 6C is a graph showing the first run of RT-QuIC analysis of hamster whole blood samples from the second hamster group.

FIG. 6D is a graph showing the second run of RT-QuIC analysis of hamster whole blood samples from the second hamster group.

FIG. 8A is a graph showing RT-QuIC analysis of serially diluted cervid brain samples.

FIG. 8B is a graph showing RT-QuIC analysis of serially diluted hamster brain samples.

DETAILED DESCRIPTION OF THE PREFERRED EMBODIMENT

Prions are present in blood and have been unknowingly transmitted to recipients of blood donations from individuals in the pre-symptomatic phase of infection. Currently there is no test to screen blood for the presence of prions. This, coupled with the requirement for human blood products in the UK to undergo intense processing for prion removal, which is less than 100% effective, has revealed a need for a diagnostic test with the ability to quickly and consistently detect low levels of prions in blood. Lack of efficient diagnostic assays also contributes to an inability to monitor animal populations for disease. It is shown herein that prions can be reliably detected in whole blood collected from various animal species infected with different strains of prions prior to the development of symptoms of disease. The application of this assay provides a means to survey blood from different populations and investigate early events associated with prion infection.

The development of a reliable in vitro blood-borne TSE-detection assay would have significant advantages for both human and animal populations and will provide techniques applicable to diagnostic assays for other protein misfolding diseases. To date, various in vitro assays have been developed with the goal of detecting prions present in blood [Orru, C. D., et al., Prion, 2012. 6(2): p. 147-52.]. These assays include sPMCA [Saa, P., J. Castilla, and C. Soto, Science, 2006. 313(5783): p. 92-4.], a ligand based assay developed to detect hematogenous prions [Terry, L. A., et al., J Virol, 2009. 83(23): p. 12552-8.], and immunoprecipitation enhanced RT-QuIC [Orrú, C. D., et al., mBio, 2011. 2(3): p. e00078-11.]. However, demonstrating satisfactory sensitivity and specificity with these assays has been a challenge.

Rapid and sensitive in vitro detection of prionemia in CWD and TME-infected hosts during both pre-clinical and clinical phases of disease is made available by the present invention, establishing the merits of a revised and improved RT-QuIC assay as an effective antemortem diagnostic tool. Early detection and screening applications will provide a means to detect asymptomatic carriers of TSE disease in the human donor blood and tissue pools, thus indicating which samples should be eliminated. The ability to detect infected blood will aid in establishing monitoring parameters for TSE intervention/therapeutic strategies and provide domestic and wildlife herd management professionals with a live test for TSE surveillance.

Example 1—RT-QuIC Analysis of Whole Blood Collected in Various Anticoagulants

Figure 1A:
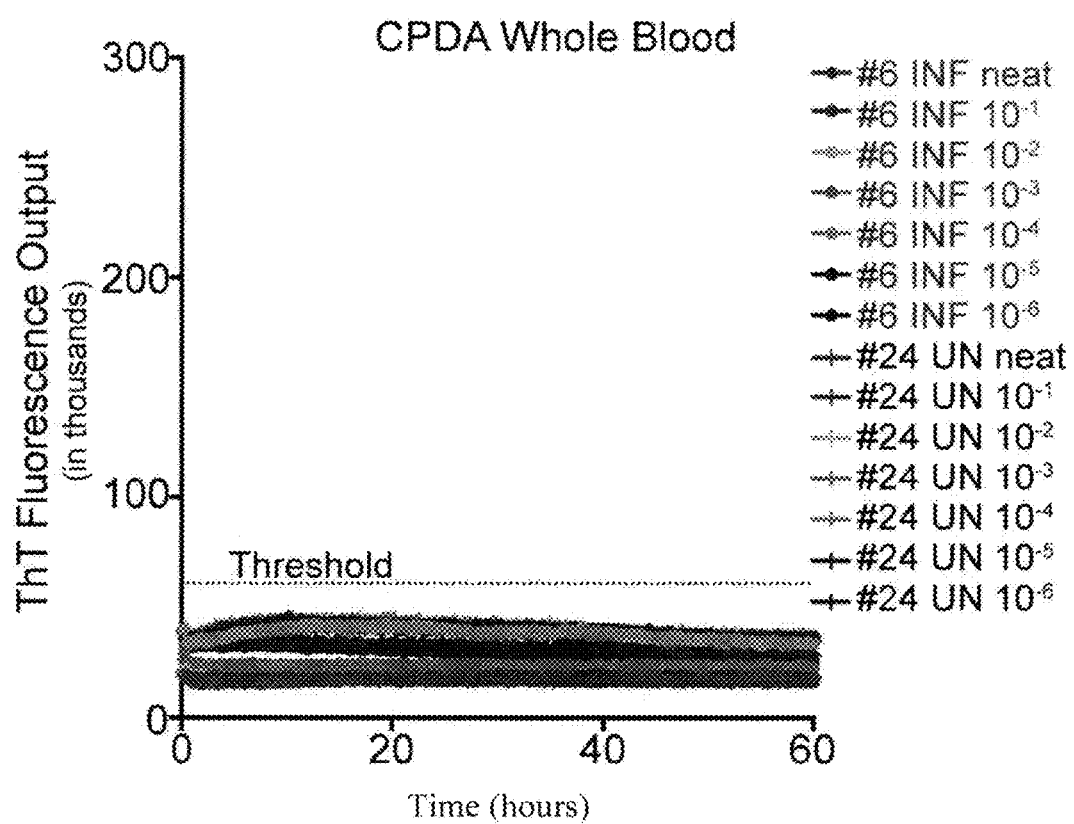
Figure 1B:
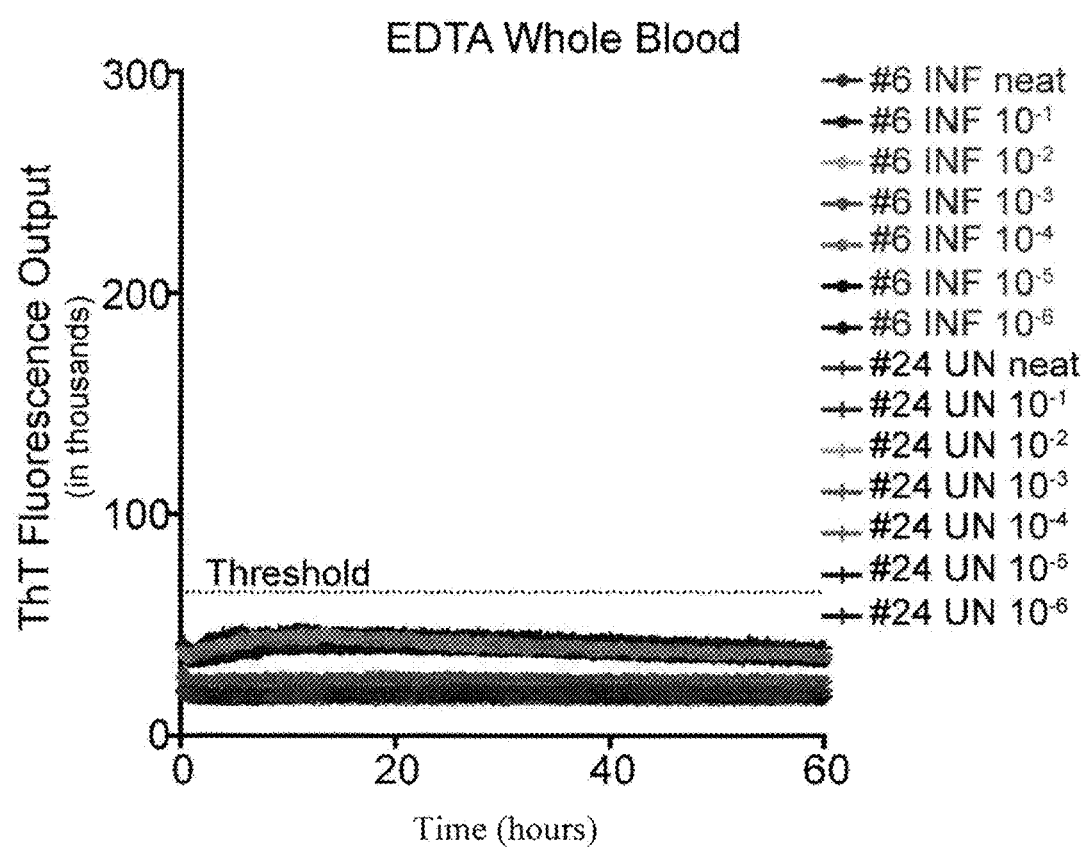
Figure 1C:
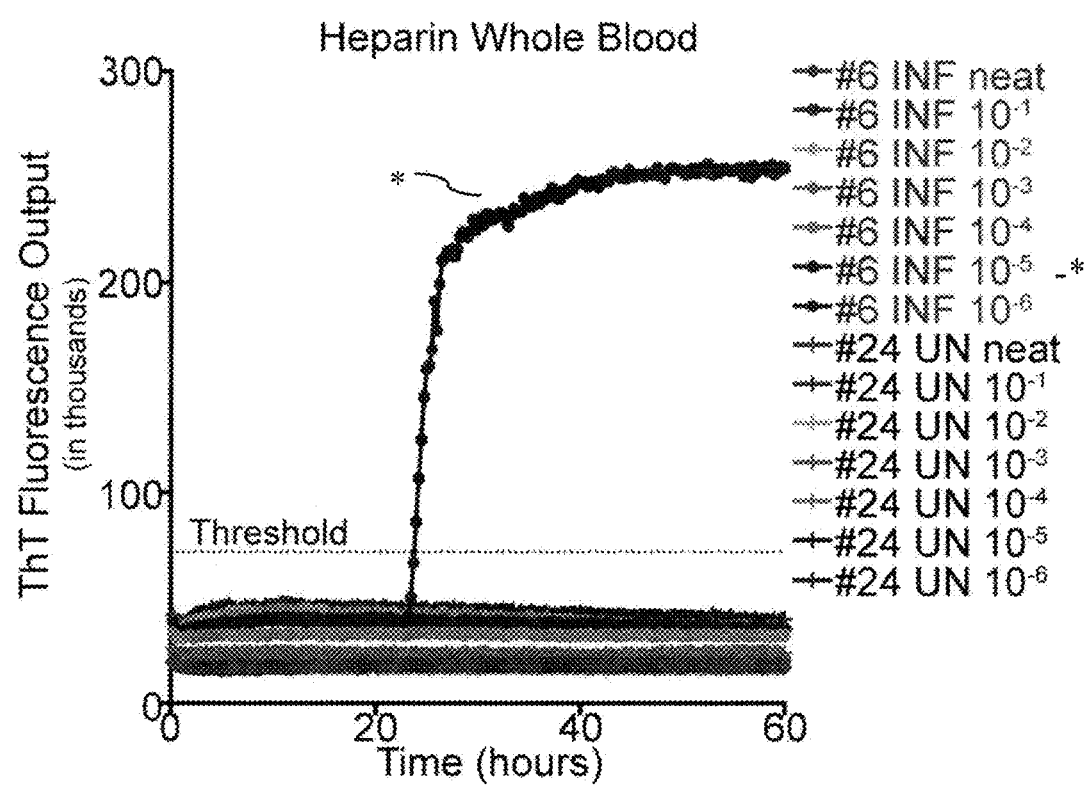

To determine the influence of common blood preservation reagents in in vitro $PrP^D$ detection assays, we compared the ability of RT-QuIC to amplify CWD prions in cervid whole blood preserved in CPDA, EDTA or heparin. Samples were run in serial dilutions ($10^0$-$10^{-6}$) in the RT QuIC assay to determine the optimal dilution for $PrP^D$ detection. While RT-QuIC $PrP^C$ converting activity was observed in heparinized blood from CWD-infected deer (½ replicates in one dilution; $10^{-5}$) (FIG. 1C), $PrP^C$ converting activity was not detected in CPDA (FIG. 1A) or EDTA (FIG. 1B) preserved blood from the same animal or any blood collected from sham-inoculated deer (FIGS. 1A-1C). All subsequent RT-QuIC analysis was conducted on whole blood harvested in heparin.

Precedence for hematogenous spread of prions via transfusion has been well established with various TSEs, including scrapie [Andreoletti, O., et al., PLoS Pathog, 2012. 8(6): p. e1002782.], CWD [Mathiason, C. K., et al., Science, 2006. 314: p. 133-136.], BSE [Houston, F., et al., Blood, 2008. 112(12): p. 4739-45.] and vCJD [Team, E., Euro Surveill, 2007. 12(1): p. E070118 4.]. To date, few in vitro assays are capable of detecting prions present in the blood of infected individuals, and those that do can suffer from decreased sensitivity due to the presence of assay inhibitors

[Castilla, J., et al., Nat Med, 2005. 11(9): p. 982-5; Terry, L. A., et al., J Virol, 2009. 83(23): p. 12552-8; Bannach, O., et al., PLoS One, 2012. 7(5): p. e36620; Edgeworth, J. A., et al., The Lancet, 2011. 377: p. 487-493.].

To assess whether anticoagulants affect $PrP^D$ detection, we analyzed whole blood collected in CPDA, EDTA and heparin. Anticoagulant storage has been shown to eliminate affect the presentation of cellular PrP, leading to the position that blood samples should be processed for detection of PrP immediately after their collection. [Glier, H. and K. Holada, J Immunol Methods, 2012. 380(1-2): p. 65-72.]. It is shown herein that whole blood collected in heparin, but not in CPDA and EDTA, elicited efficient in vitro RT-QuIC prion conversion.

Example 2—RT-QuIC Analysis of Fresh Versus Frozen Whole Blood

Figure 2A:
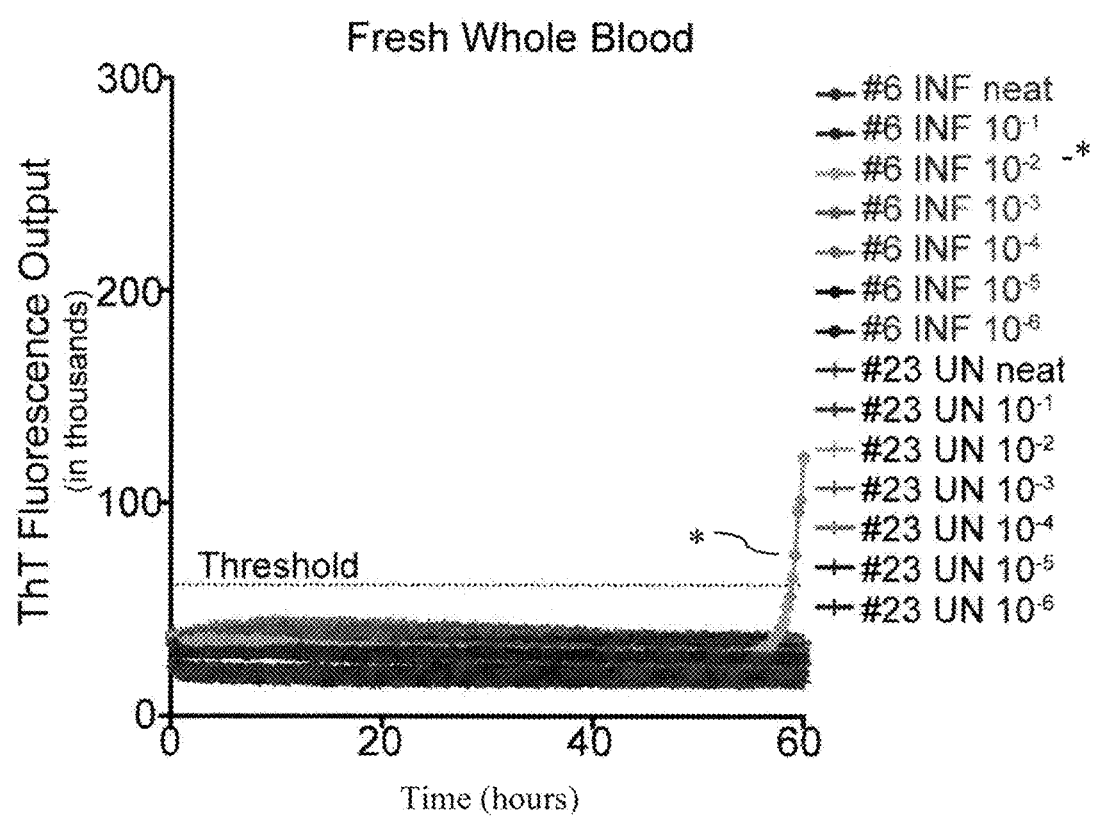
Figure 2B:
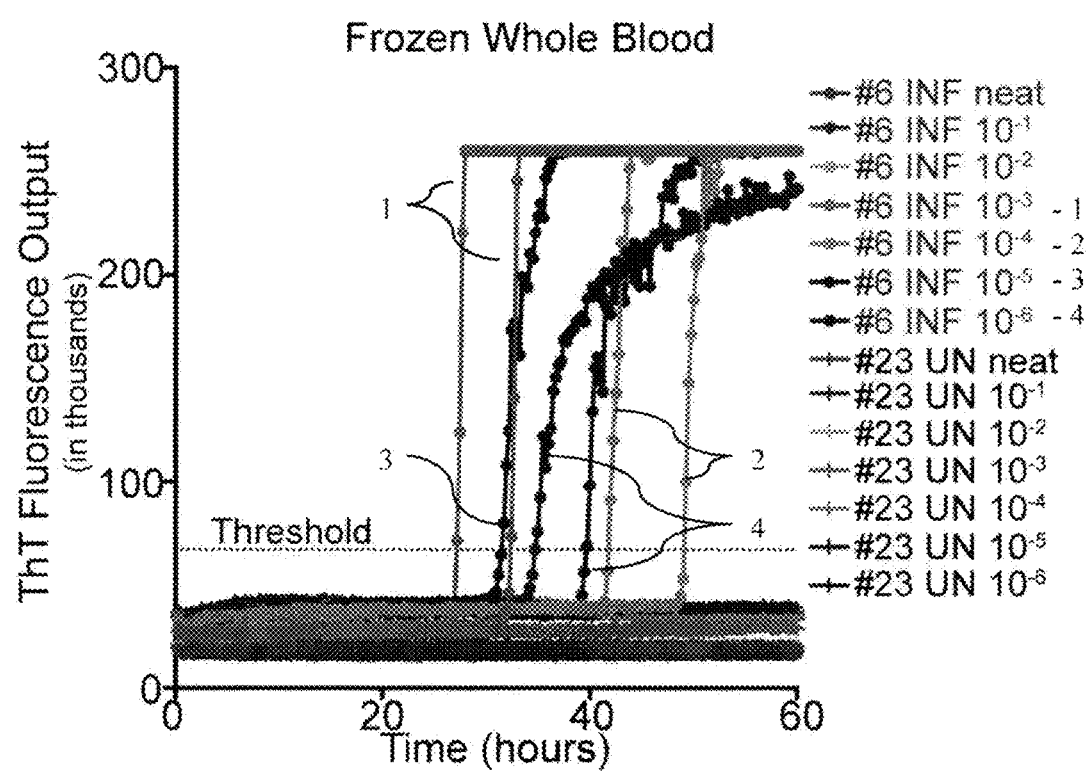

In order to determine if historical blood samples were adequately preserved to initiate $PrP^C$ converting activity in RT-QuIC, whole blood was collected from contemporary naïve and CWD112 infected white-tailed deer and compared as fresh versus frozen samples. Samples were processed in various dilutions ranging from undiluted to $10^{-6}$ to determine the optimal dilution for $PrP^D$ detection using frozen whole blood in the RT-QuIC assay. While $PrP^C$ converting activity was detected in fresh whole blood (FIG. 2A), blood that had been processed through the freeze-thaw procedure yielded higher and more consistent detection of prion converting activity (2/2 replicates in each of four dilutions) (FIG. 2B). $PrP^C$ converting activity was not observed in wells containing only substrate or naïve cervid blood. All subsequent RT-QuIC analysis included heparinized whole blood that had undergone four freeze-thaw cycles.

To assess the feasibility of using historical frozen samples for future analysis of blood-borne prions, the effects of freezing blood prior to RT-QuIC was evaluated. It is demonstrated herein that the freeze-thaw cycle enhances RT-QuIC blood-borne prion detection sensitivity, facilitating in vitro prion detection at earlier time points with a more robust amplification than samples that did not undergo the freeze-thaw process. There is evidence for the accumulation of aggregated misfolded prion isoforms in the cytoplasm of infected cells [Hofmann, J. P., et al., Proc Natl Acad Sci USA, 2013. 110(15): p. 5951-6.]. One possible result is that these aggregates are released from the cell as lysis occurs. Thermal shock on whole blood samples damages the cell membrane and initiates hemolysis [Lovelock, J. E., Nature, 1954. 173(4406): p. 659-61; Lovelock, J. E., Br J Haematol, 1955. 1(1): p. 117-29.], which is thought to release intracellular components. While not intending to be bound by any theory, cell lysis of blood collected from TSE-infected animals, associated with repeated freeze-thaw cycles may liberate sufficient prions to enhance in vitro nucleation and thus the detection of $PrP^C$ converting activity.

Figure 3A:
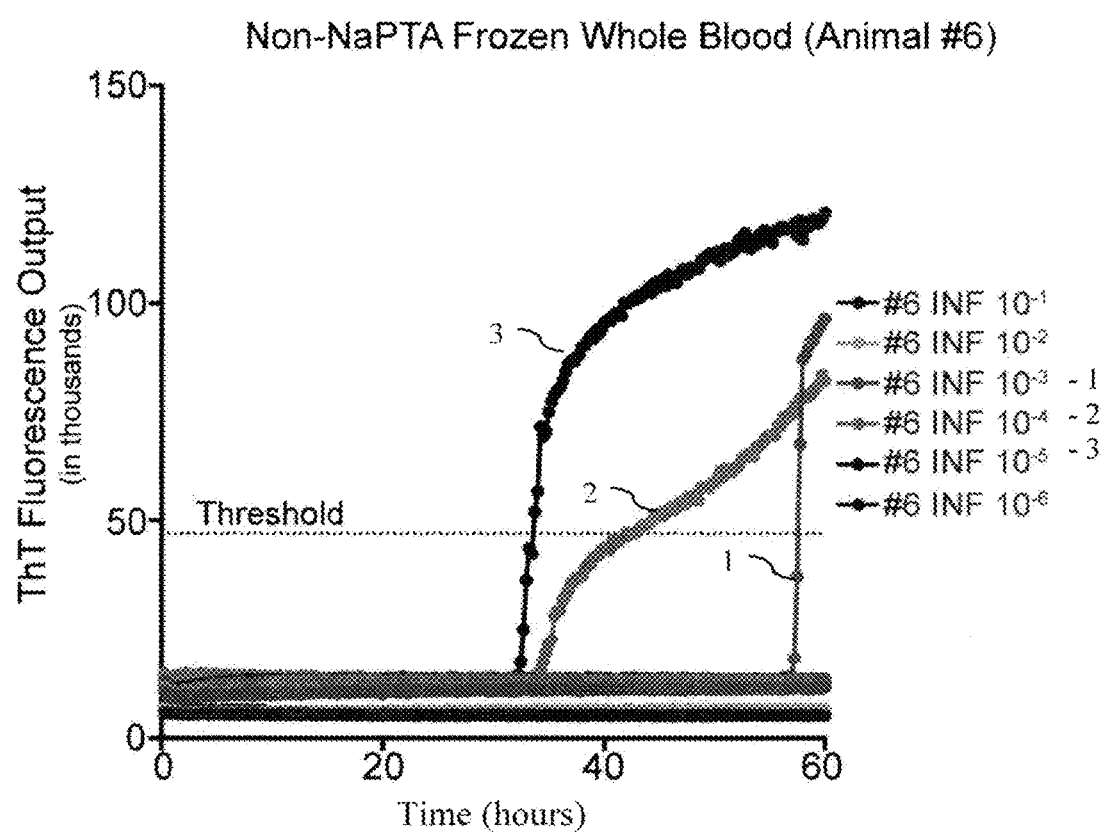
Figure 3B:
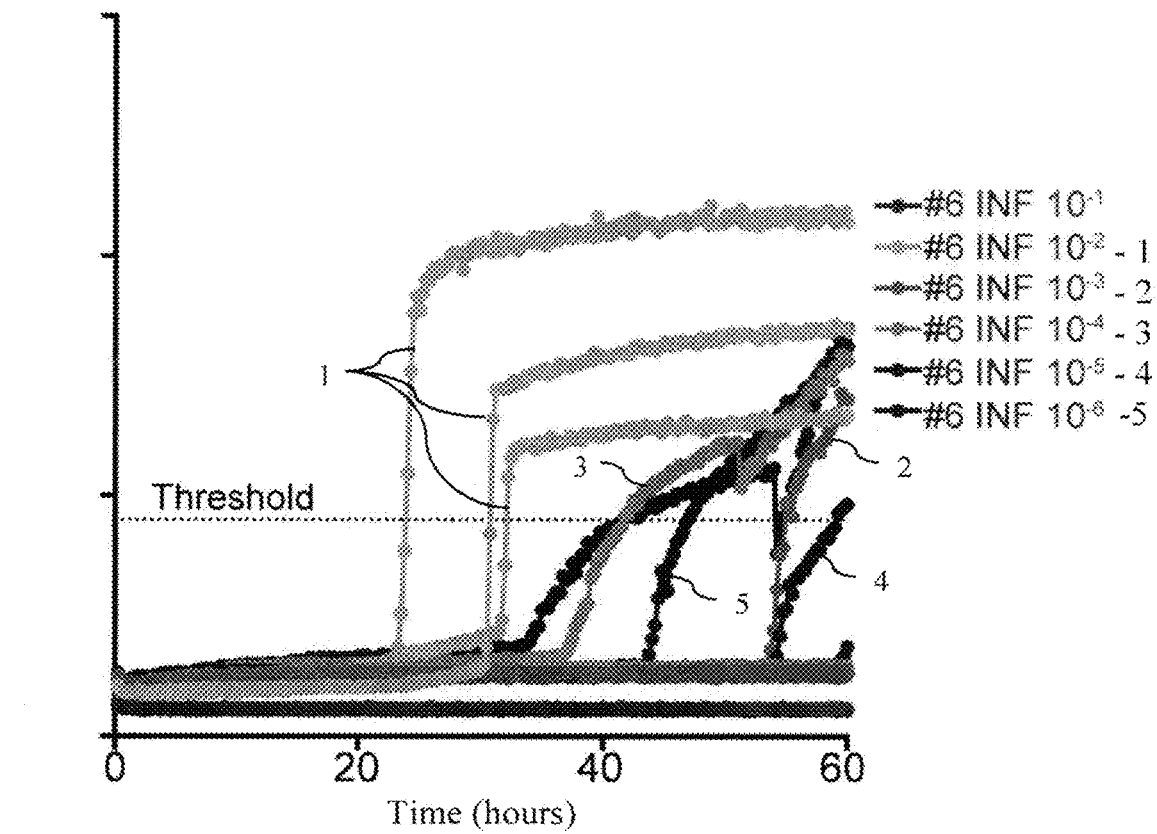
Figure 3C:
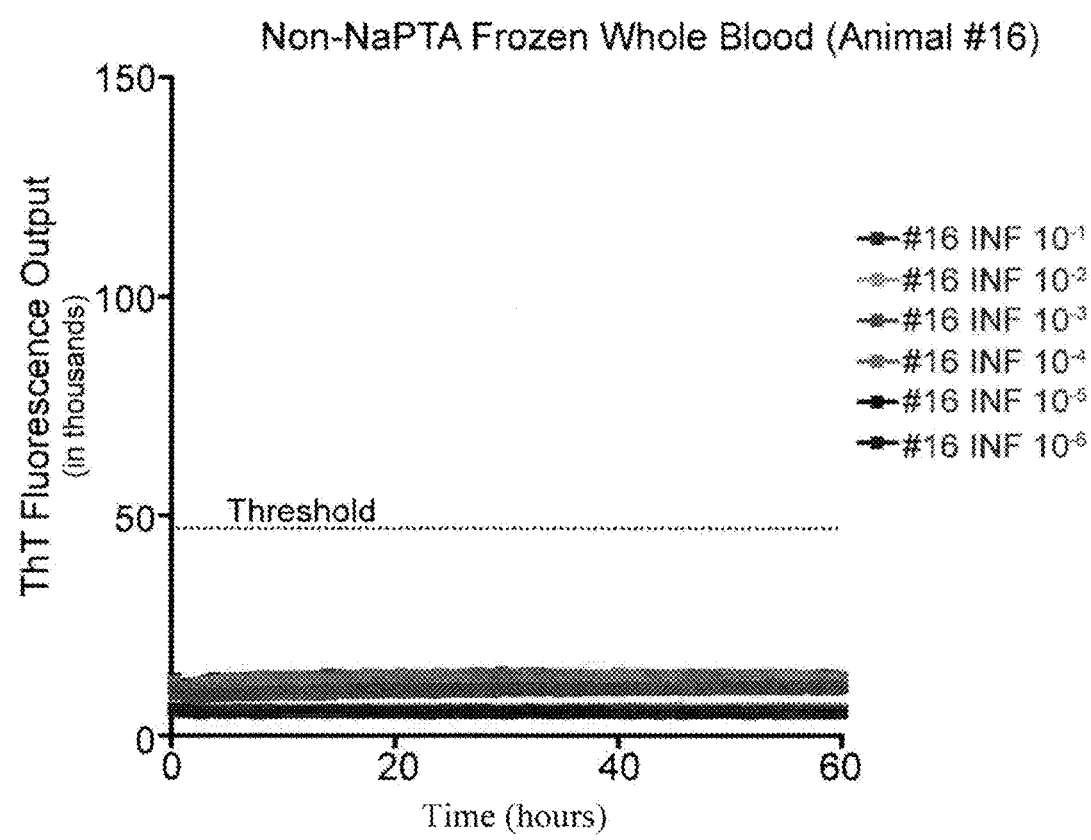
Figure 3D:
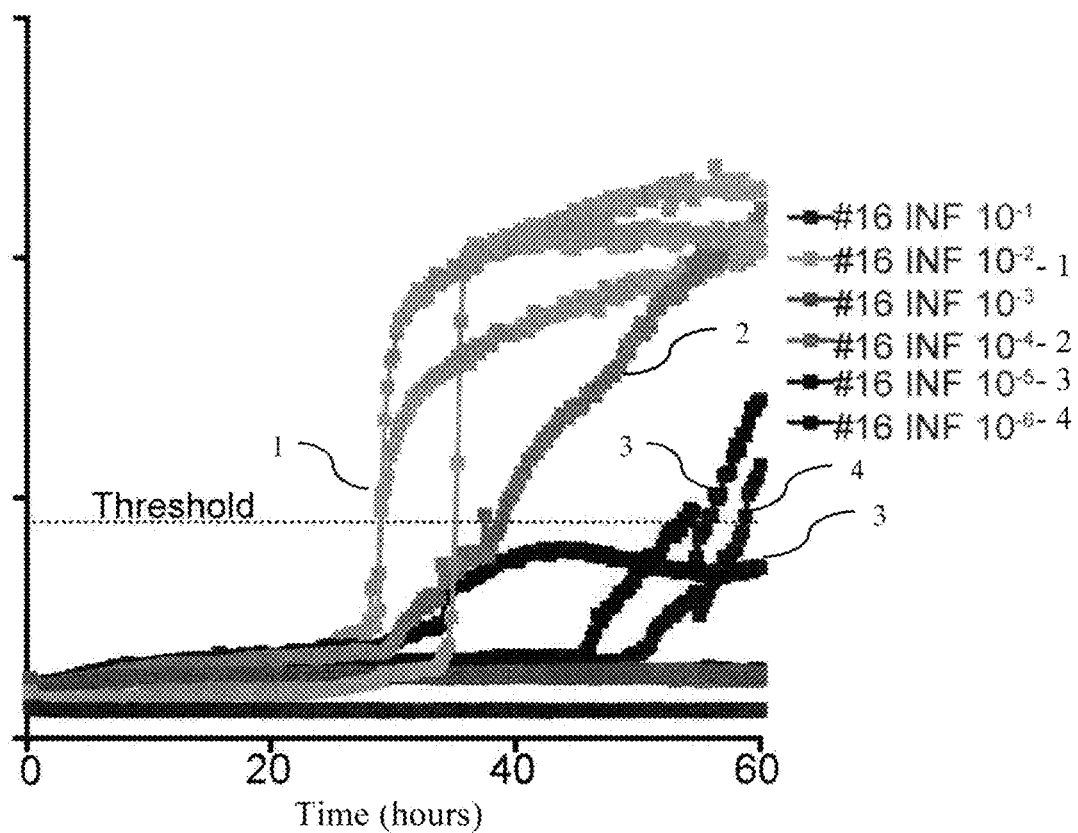
Figure 3E:
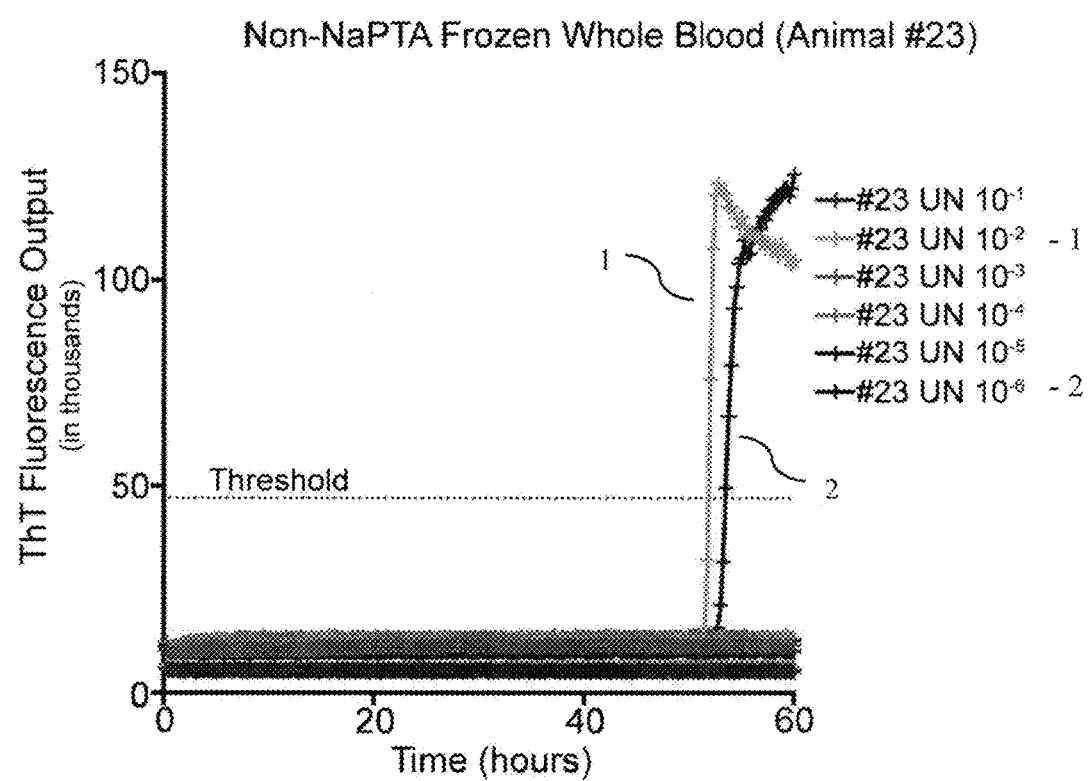
Figure 3F:
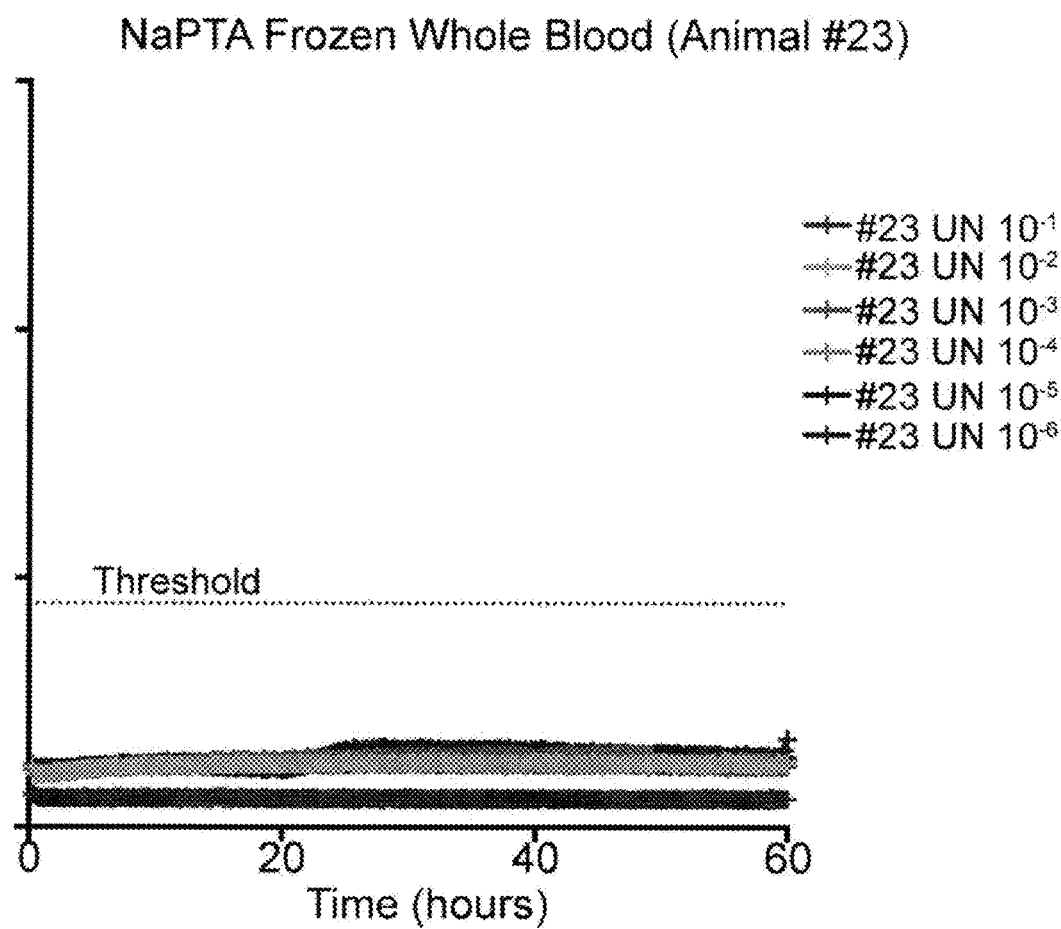

Example 3—Effects of Sodium Phosphotungstic Acid Precipitation (NaPTA) on RT-QuIC $PrP^D$ Detection NaPTA precipitation was applied to heparinized whole blood that had undergone freeze-thaw cell lysis in an attempt to increase both the sensitivity and specificity of the RT-QuIC assay. With the improved sensitivity and specificity provided by NaPTA pretreatment, reliable RT-QuIC results at a $10^{-2}$ dilution of CWD-infected whole blood was demonstrated (FIGS. 3A-3D), while NaPTA treated whole blood from a naïve individual remained conversion free (FIGS. 3E and 3F).

Thus, all of the remaining RT-QuIC analyses of TSE prion converting activity in historical and contemporary samples were conducted with heparinized and freeze-thawed NaPTA-treated whole blood.

Components present in bodily fluids may interfere with or inhibit prion conversion and thus in vitro detection of the aberrant form of the prion protein [Barria, M. A., et al., Methods Mol Biol, 2012. 849: p. 199-212.]. Using immunoprecipitation coupled with RT-QuIC, Orrú et al. [Orrú, C. D., et al., mBio, 2011. 2(3): p. e00078-11.] was able to establish in vitro detection of $PrP^C$ converting activity in plasma and serum samples from scrapie-infected hamsters. Using NaPTA precipitation we were able to concentrate hematogenous prions to a more detectable level and/or remove assay inhibitors, augmenting the ability to directly detect prions in whole blood.

With the application of an anticoagulant that facilitates prion conversion in vitro, the freeze-thaw cell lysis and NaPTA precipitation, an RT-QuIC assay for efficient detection of $PrP^D$ in whole blood samples, as taught herein, is now possible. The new protocol can be referred to as whole blood optimized (WBO) RT-QuIC. NaPTA precipitation increased the number of positive replicates and decreased the assay time required to initiate $PrP^C$ conversion/detection in whole blood harvested from TSE-infected animals, while limiting false positive $PrP^C$ converting activity in samples from uninfected animals.

Figure 4:
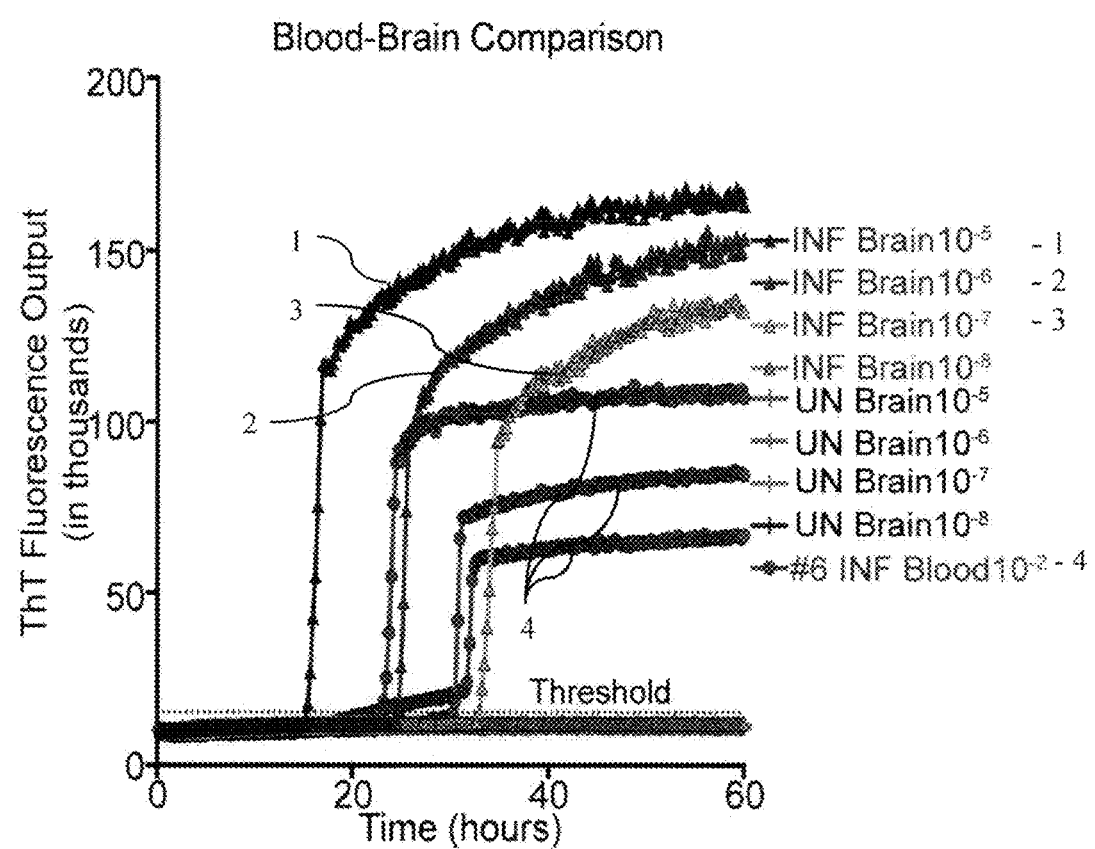
Figure 5A:
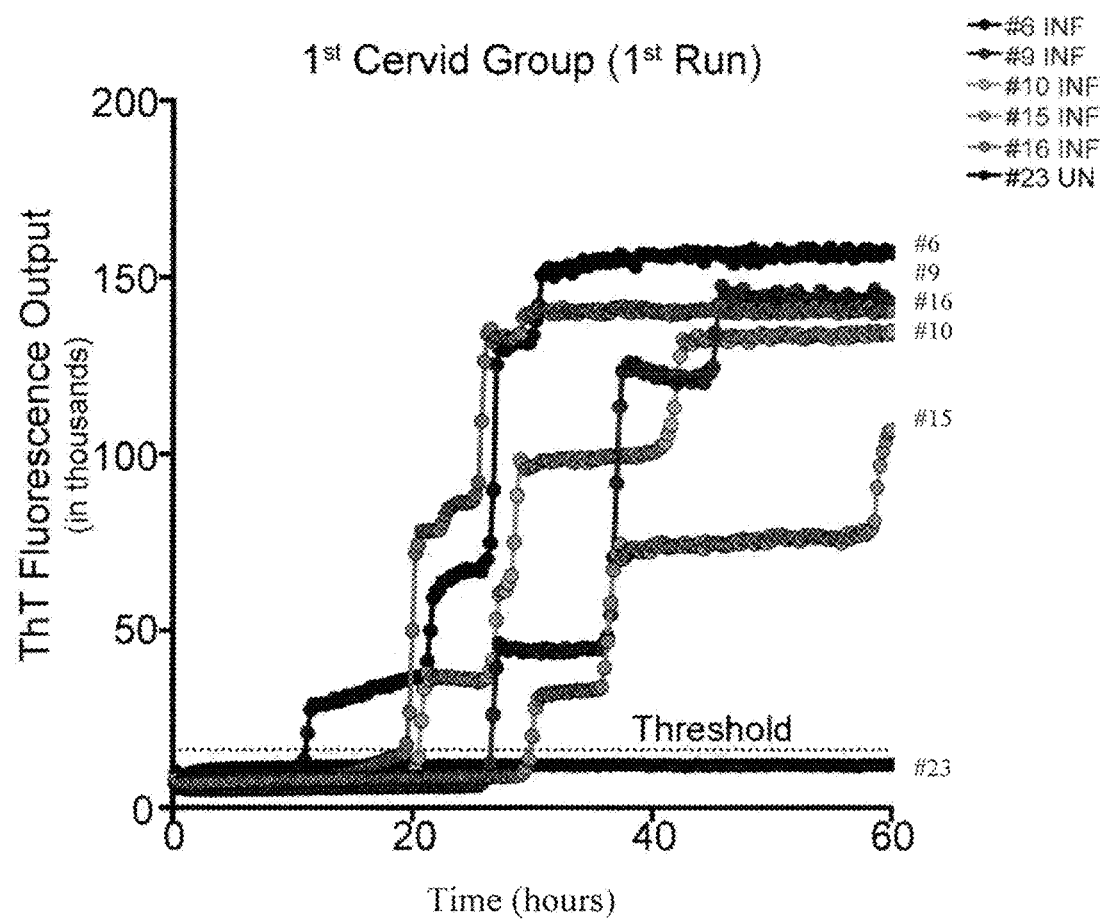
FIG. 5C is a graph showing the first run of RT-QuIC analysis of cervid whole blood samples from the second cervid group.
FIG. 5D is a graph showing the second run of RT-QuIC analysis of cervid whole blood samples from the second cervid group.
FIG. 5E is a graph showing the first run of RT-QuIC analysis of cervid whole blood samples from the third cervid group.
FIG. 5F is a graph showing the second run of RT-QuIC analysis of cervid whole blood samples from the third cervid group.
Figure 5B:
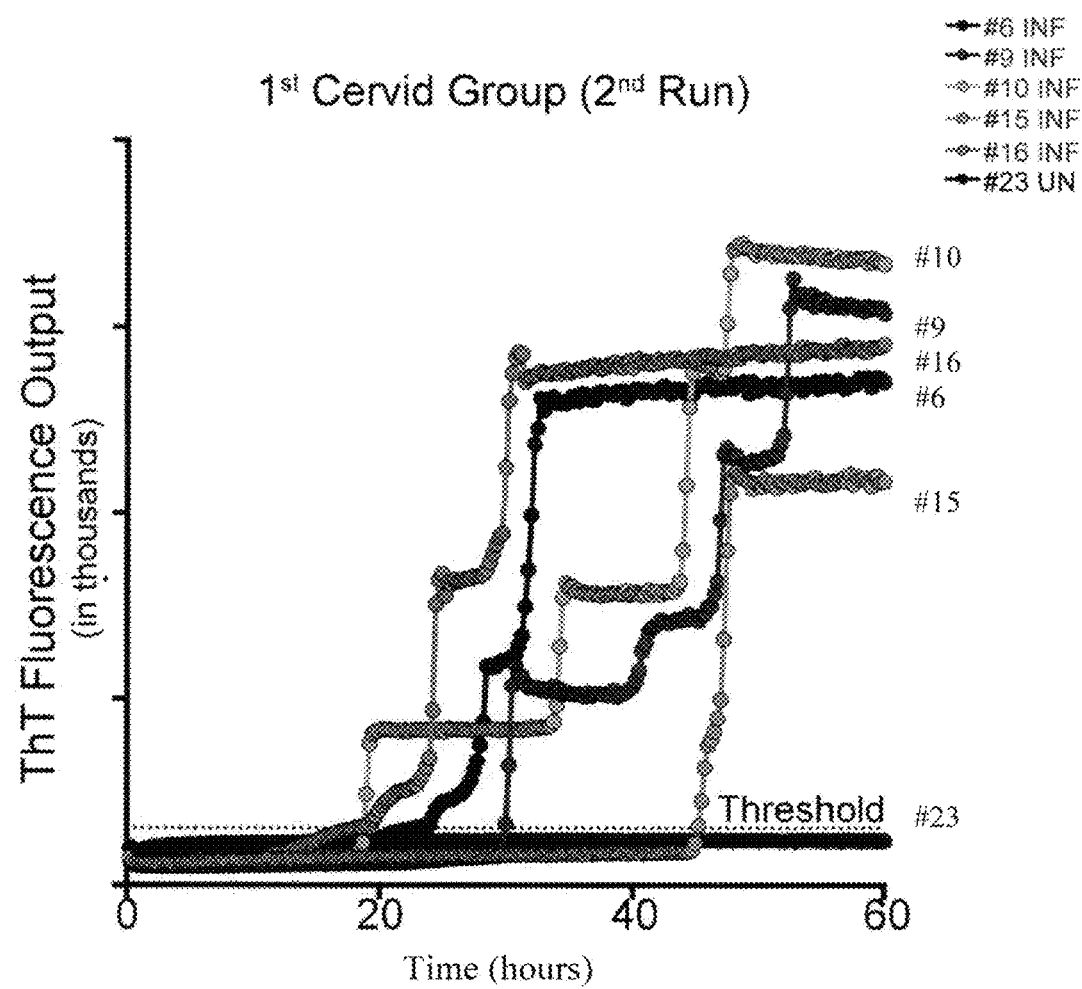
Figure 5C:
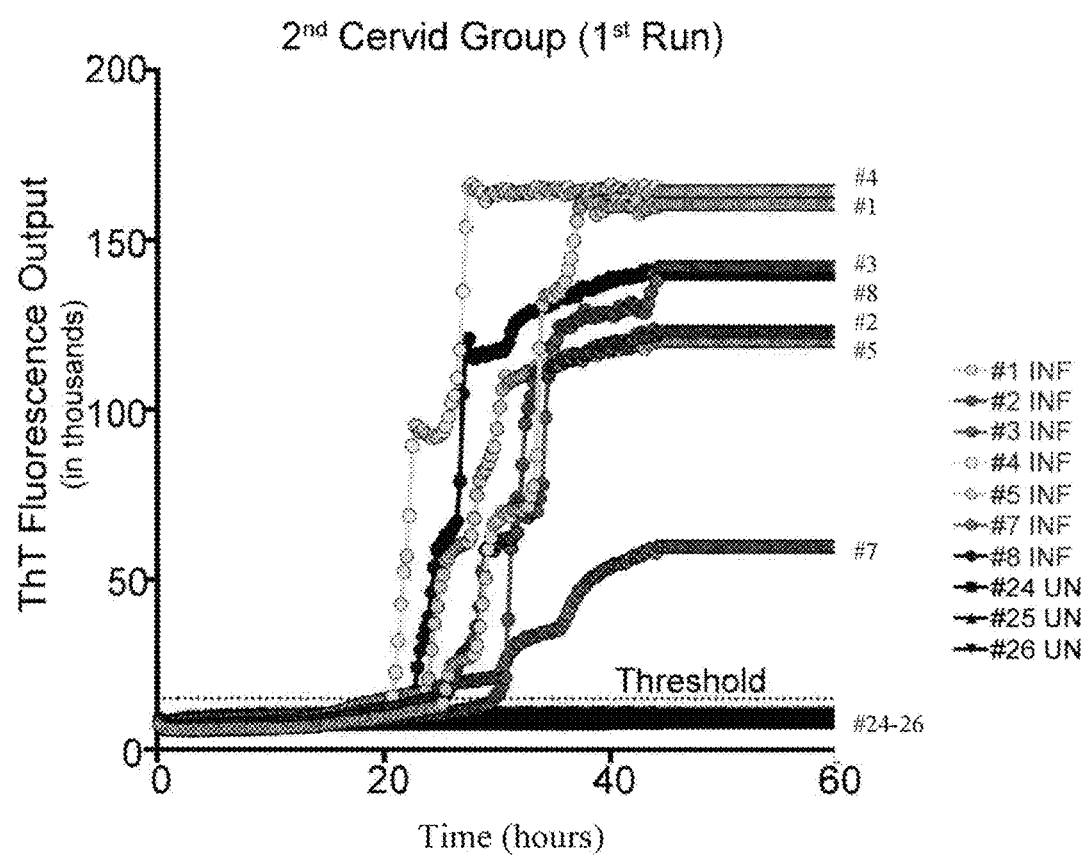
Figure 5D:
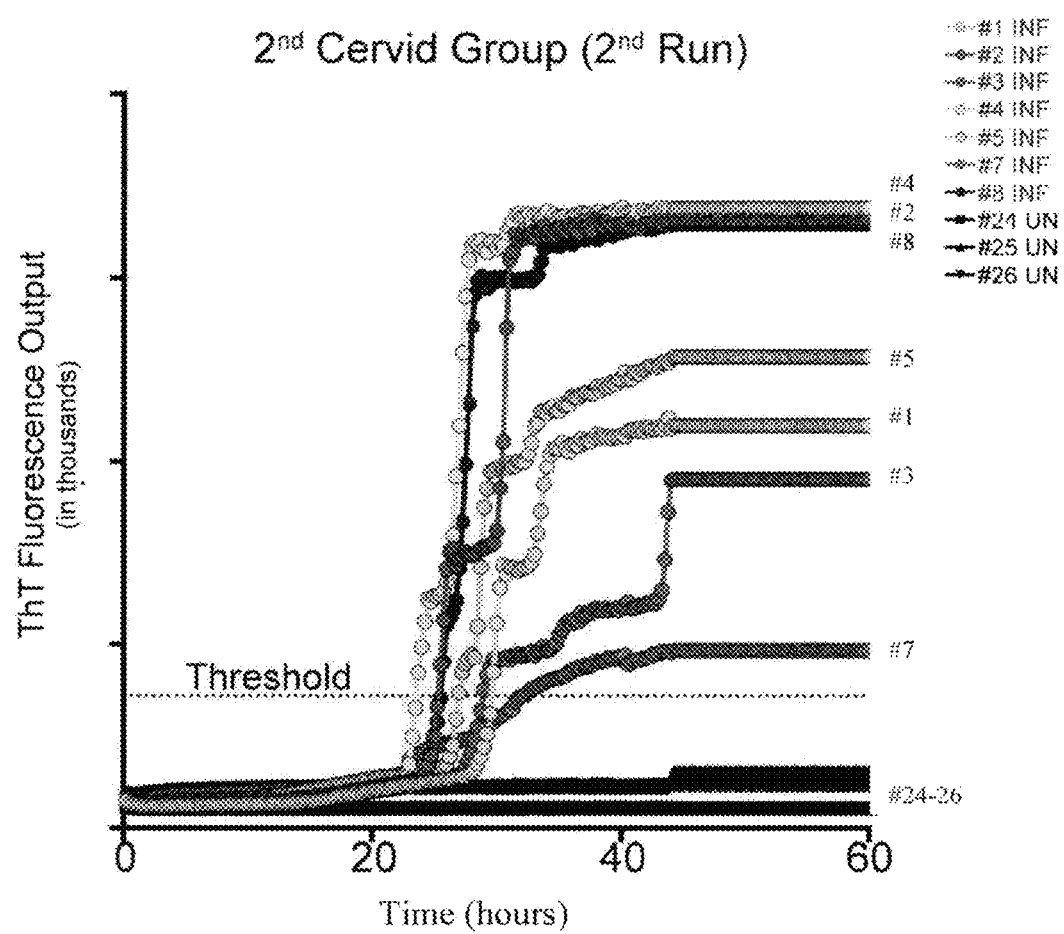
Figure 5E:
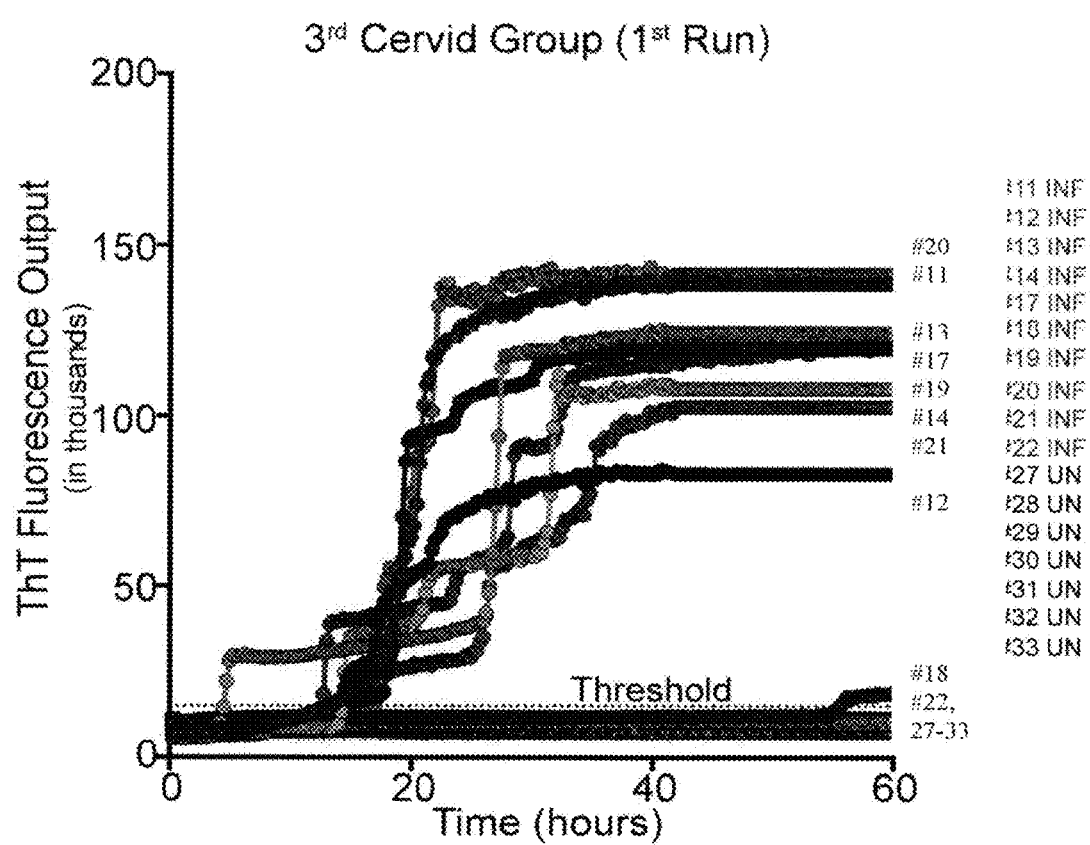
Figure 5F:
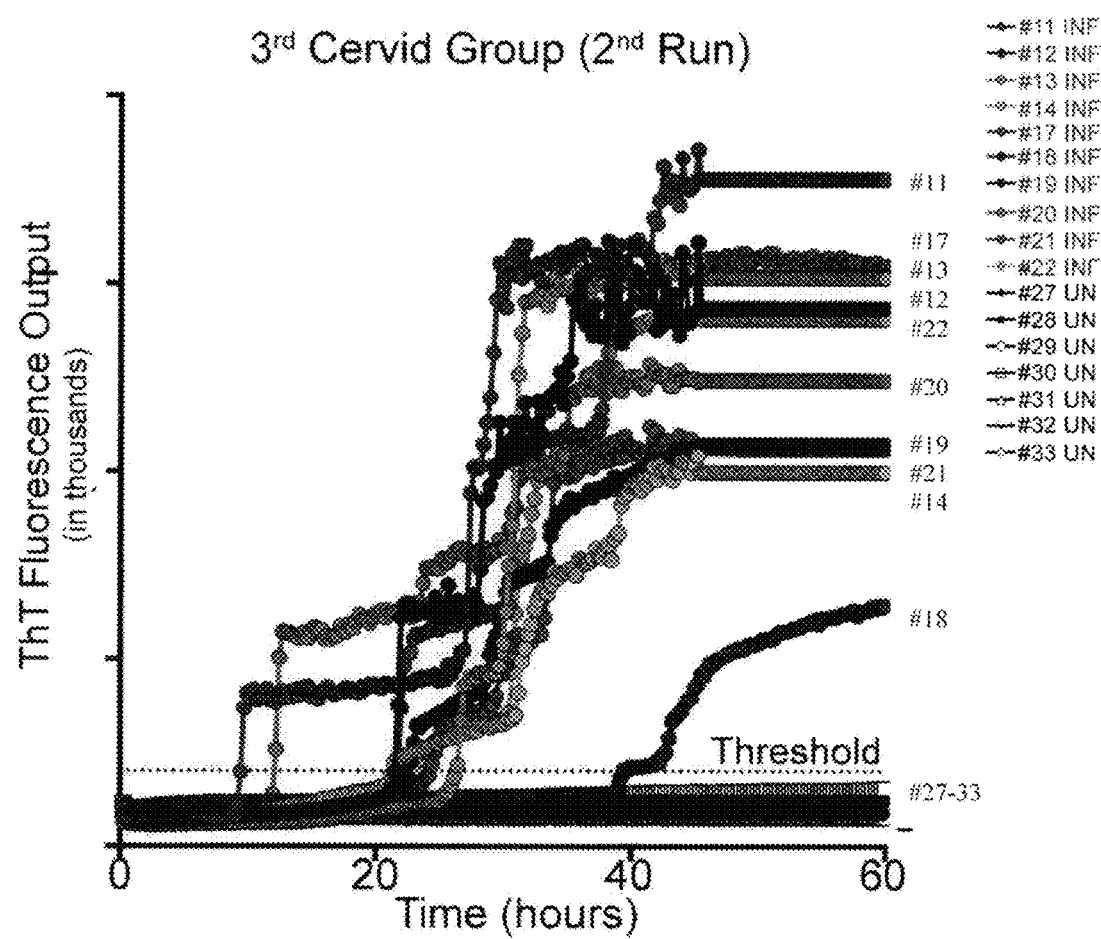

Example 4—RT-QuIC Comparison of CWD-Positive Brain Versus NaPTA Concentrated Whole Blood To evaluate the levels of $PrP^D$ present in NaPTA concentrated whole blood samples, $PrP^C$ converting activity was compared to that detected in serial dilutions of CWD-positive white tailed deer brain (FIG. 4). NaPTA treated whole blood (10 ml starting volume of whole blood) diluted to $10^{-2}$ demonstrated $PrP^D$ levels approximately equivalent to that measured in $10^{-6}$-$10^{-7}$ dilution of CWD-positive brain. Equivalence was determined by comparison of the time to positivity for whole blood and brain samples.

Many groups have developed quantitative in vitro methodologies to analyze the levels of $PrP^D$ present in various tissues and bodily fluid samples. Murayama et al. [Murayama, Y., et al., J Gen Virol, 2007. 88(Pt 10): p. 2890-8.] used PMCA to establish a direct comparison of $PrP^D$ levels in buffy coat and plasma to $PrP^D$ levels seen in serial dilutions of TSE-infected brain by analyzing which round of PMCA samples began demonstrating positivity. Other laboratories [Chen, B., et al., Nature Methods, 2010. 7(7): p. 519-521; Gonzalez-Romero, D., et al., FEBS Lett, 2008. 582(21-22): p. 3161-6.] have reported quantitative and semi-quantitative methods of PMCA to determine the levels of $PrP^D$ in blood and urine by comparing to the amount of amplifiable $PrP^D$ present in TSE-infected brain. Castilla et al. [Castilla, J., et al., Nat Med, 2005. 11(9): p. 982-5.] were able to demonstrate that PMCA amplifiable prions in buffy coat collected from 1 ml of scrapie-adapted hamster blood contained roughly 0.1-1 pg of $PrP^D$ molecules. Our RT-QuIC results indicate that 2 µl of a $10^{-2}$ dilution (0.5 ml of whole blood NaPTA precipitated 10-fold, further diluted to $10^{-2}$) contained $PrP^D$ levels equivalent to those seen in 0.2 ng-2 ng of CWD-positive brain.

Example 5—Detection of Prion Converting Activity in CWD-Infected Cervid Whole Blood Twenty-two of 22 clinical and sub-clinical CWD-infected cervids (16 white-tailed deer and 6 muntjac deer) and 0/11 naive cervids (5 white-tailed deer and 6 muntjac deer) exhibited RT-QuIC PrPc converting activity in 7/8 or 8/8 replicates within 60 hours (FIGS. 5A-5F, Table 1). Sample replicates were averaged on each plate and a positive threshold was set at five times the standard deviation of the negative control average.

TABLE 1

Cervid blood donor inoculation, clinical status, and assay results

| Animal # | Inoculum | Route of Inoculation | Disease Status | Western Blot Status (Obex) | IHC Status | Positive QuIC Replicates |
|---|---|---|---|---|---|---|
| 1 (WTD) | 2 ml 5% CWD+ brain homogenate | Aerosol | Clinical | + | $+^B$ | 8/8 |
| 2 (WTD) | 2 ml 5% CWD+ brain homogenate | Aerosol | Clinical | + | $+^B$ | 8/8 |
| 3 (WTD) | 2 ml 5% CWD+ brain homogenate | Aerosol | Clinical | + | $+^B$ | 7/8 |
| 4 (WTD) | 2 ml 5% CWD+ brain homogenate | Aerosol | Clinical | + | $+^B$ | 8/8 |
| 5 (WTD) | 2 ml 5% CWD+ brain homogenate | Aerosol | Sub-clinical | + | $+^B$ | 8/8 |
| 6 (WTD) | 2 ml 5% CWD+ brain homogenate | Aerosol | Clinical | + | $+^B$ | 8/8 |
| 7 (WTD) | 1.0 g 10% CWD+ brain homogenate | PO | Sub-clinical | ND | $+^B$ | 7/8 |
| 8 (WTD) | 1.0 g 10% CWD+ brain homogenate | PO | Sub-clinical | + | $+^B$ | 8/8 |
| 9 (WTD) | 1.0 g 10% CWD+ brain homogenate | PO | Sub-clinical | − | $-^B$ | 7/8 |
| 10 (WTD) | 1.0 g 10% CWD+ brain homogenate | PO | Sub-clinical | + | $+^B$ | 8/8 |
| 11 (WTD) | 1.0 g 10% CWD+ brain homogenate | PO | Sub-clinical | + | $+^B$ | 8/8 |
| 12 (WTD) | 1.0 g 10% CWD+ brain homogenate | PO | Clinical | + | $+^B$ | 7/8 |
| 13 (WTD) | 1.0 g 10% CWD+ brain homogenate | PO | Clinical | + | $+^B$ | 8/8 |
| 14 (WTD) | 1.0 g 10% CWD+ brain homogenate | PO | Sub-clinical | + | $+^B$ | 7/8 |
| 15 (WTD) | 2.0 g 10% CWD+ brain homogenate | IC | Clinical | + | $+^{B,O}$ | 7/8 |
| 16 (WTD) | 250 ml 5% CWD+ whole blood | IV | Clinical | + | $+^{B,O}$ | 8/8 |
| 17 (MJ) | 1.0 g 10% CWD+ brain homogenate | PO/SQ | Sub-clinical* | − | $+^O$ | 8/8 |
| 18 (MJ) | 1.0 g 10% CWD+ brain homogenate | PO/SQ | Sub-clinical* | − | $+^O$ | 6/8 |
| 19 (MJ) | 1.0 g 10% CWD+ brain homogenate | PO/SQ | Clinical | + | $+^{B,O}$ | 8/8 |
| 20 (MJ) | 1.0 g 10% CWD+ brain homogenate | PO/SQ | Clinical | + | $+^{B,O}$ | 8/8 |
| 21 (MJ) | 1.0 g 10% CWD+ brain homogenate | PO/SQ | Clinical | + | $+^{B,O}$ | 8/8 |
| 22 (MJ) | 1.0 g 10% CWD+ brain homogenate | PO/SQ | Clinical | + | $+^{B,O}$ | 4/8 |
| 23 (WTD) | 2 ml sham homogenate | Aerosol | NA | − | $-^B$ | 0/8 |
| 24 (WTD) | 2 ml sham homogenate | Aerosol | NA | − | $-^B$ | 0/8 |
| 25 (WTD) | 2 ml sham homogenate | Aerosol | NA | − | $-^B$ | 0/8 |
| 26 (WTD) | CWD - urine/feces | PO | NA | − | $-^{B,O}$ | 0/8 |
| 27 (WTD) | CWD - urine/feces | PO | NA | − | $-^{B,O}$ | 0/8 |
| 28 (MJ) | 1.0 g sham homogenate | PO/SQ | NA | − | $-^O$ | 0/8 |
| 29 (MJ) | 1.0 g sham homogenate | PO/SQ | NA | − | $-^O$ | 0/8 |
| 30 (MJ) | 1.0 g sham homogenate | PO/SQ | NA | − | $-^O$ | 0/8 |

TABLE 1-continued

Cervid blood donor inoculation, clinical status, and assay results

| Animal # | Inoculum | Route of Inoculation | Disease Status | Western Blot Status (Obex) | IHC Status | Positive QuIC Replicates |
|---|---|---|---|---|---|---|
| 31 (MJ) | Uninoculated | NA | NA | – | –[O] | 0/8 |
| 32 (MJ) | Uninoculated | NA | NA | – | –[O] | 0/8 |
| 33 (MJ) | Uninoculated | NA | NA | – | –[O] | 0/8 |

WTD = White-tailed deer
MJ = Muntjac deer
ND = Not Done
NA = Not Available
– = $PrP^D$ was not detected in the sample
+ = $PrP^D$ was detected in the sample
[B] = Biopsy of tonsil and recto-anal mucosa associated lymphoid tissue
[O] = Obex
* = Less than halfway to clinical disease RT-QuIC assay has the ability to detect prions in tissue samples with similar sensitivity as bioassay (~1 lethal dose), rendering it appropriate for the detection of $PrP^D$ in bodily fluids such as blood and saliva [Wilham, J. M., et al., PLoS Pathog, 2010. 6(12): p. e1001217.]. RT-QuIC assay efficacy for CWD-infected whole blood was evaluated following pretreatment to augment the release of prions from carrier cells and minimize inhibitory factors (freeze-thaw/NaPTA). We have demonstrated that our novel and improved RT-QuIC assay is sufficiently sensitive to detect $PrP^C$ converting activity in whole blood harvested from pre-clinical and clinical IHC/Western blot-confirmed CWD-infected animals. Furthermore, our RT-QuIC assay has demonstrated the ability to detect $PrP^C$ converting activity in CWD-inoculated animals prior to the mid point between inoculation and clinical disease.

Using PMCA for the detection of $PrP^D$ in the blood of scrapie-infected hamsters, Saa et al. [Saa, P., et al., Science, 2006. 313(5783): p. 92-4.] reported sensitivity levels of 80% for clinical animals, and up to 60% for pre-clinical animals. Orris et al. demonstrated even greater sensitivity for $PrP^D$ in blood plasma of scrapie-infected hamsters using immuno-precipitation coupled with RT-QuIC [Orrú, C. D., et al., mBio, 2011. 2(3): p. e00078-11.]. Utilizing the improved RT QuIC assay for cervid whole blood as taught herein, we have exhibited sensitivity levels of 93.8% for clinical animals, and 92.2% for sub-clinical animals while maintaining 100% specificity for both groups. These results reveal the potential of RT-QuIC as a reliable in vitro assay for blood-borne prion detection.

Figure 6A:
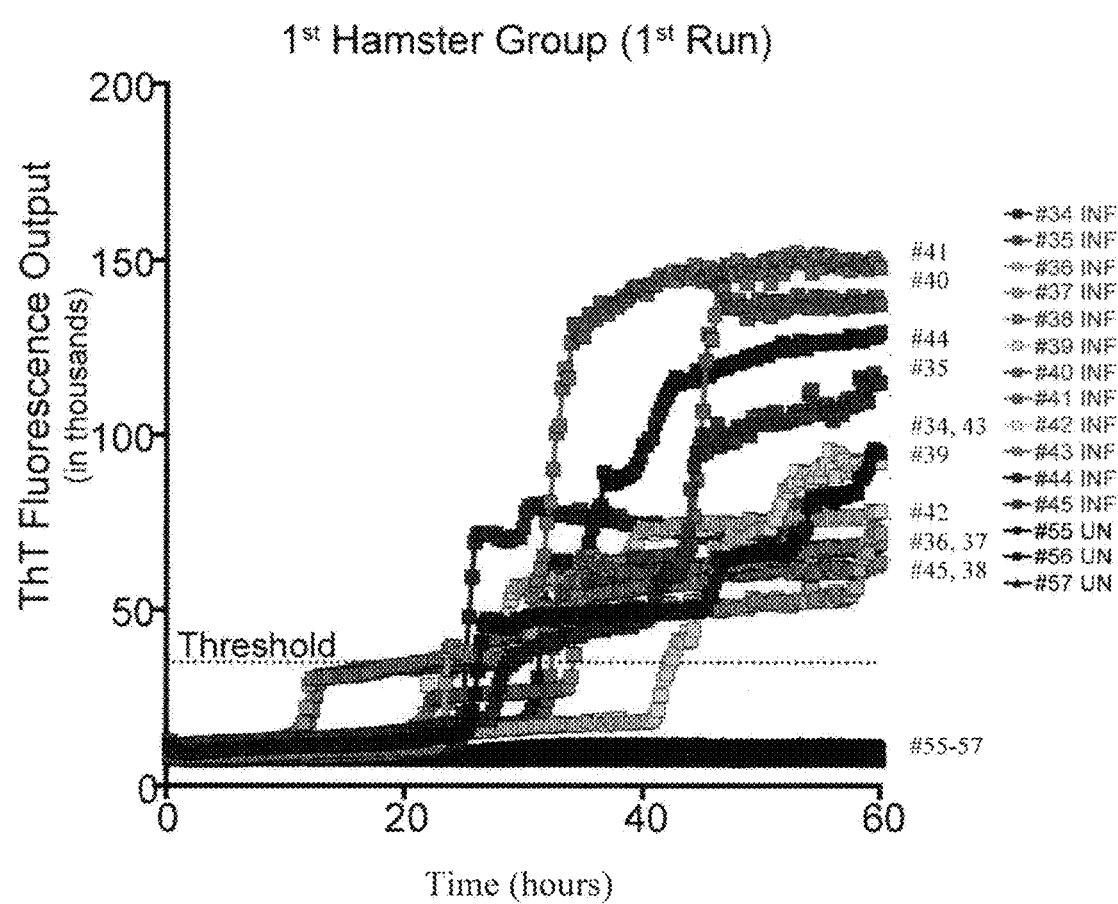
FIGS. 6A-6D are a series of four graphs showing RT-QuIC analysis of hamster whole blood samples. Blood samples were diluted to $10^{-2}$ and 8 replicates were analyzed over 2 experiments of 60 hours, and positivity was determined by ThT fluorescence level above threshold. $PrP^C$ converting activity is demonstrated in 21 TME-infected blood samples, and is absent in all TME-naïve samples (A-D). Each line is the average of four replicates for a specific animal. UN=Uninfected; INF=Infected.
Figure 6B:
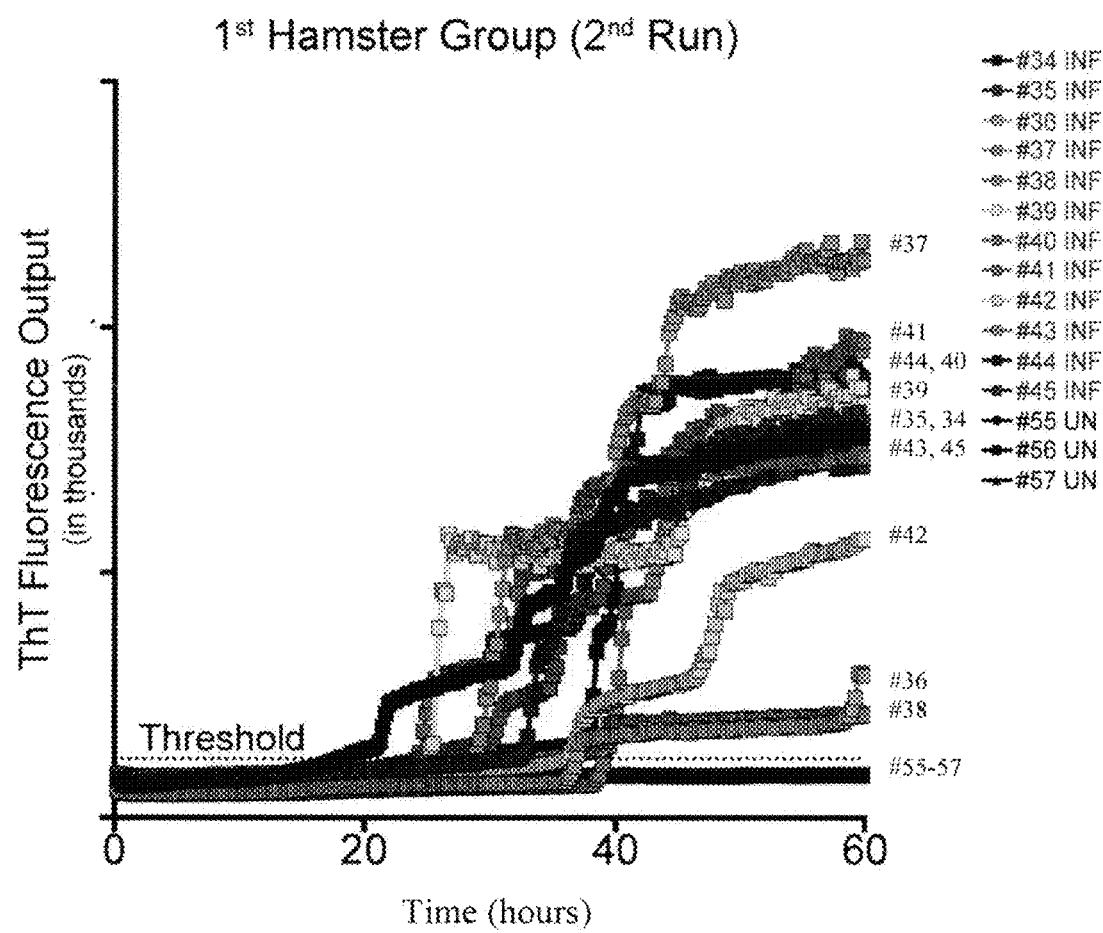
Figure 6C:
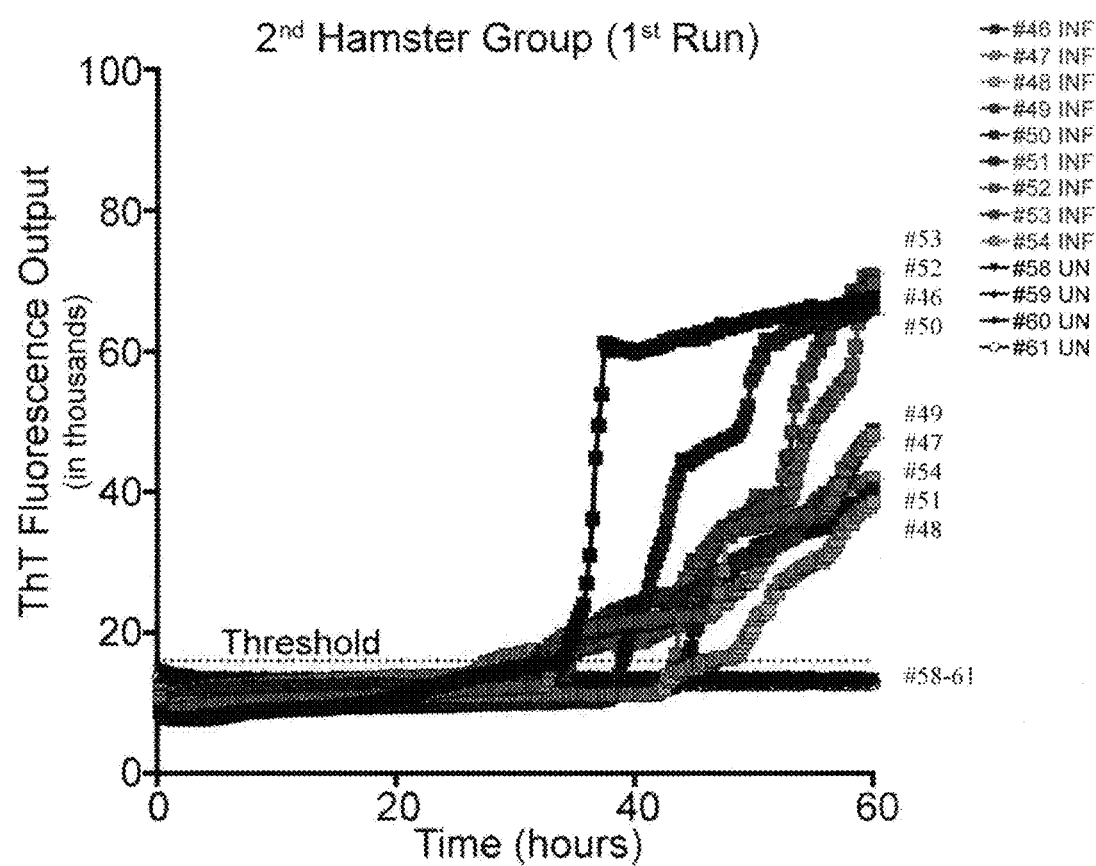
Figure 6D:
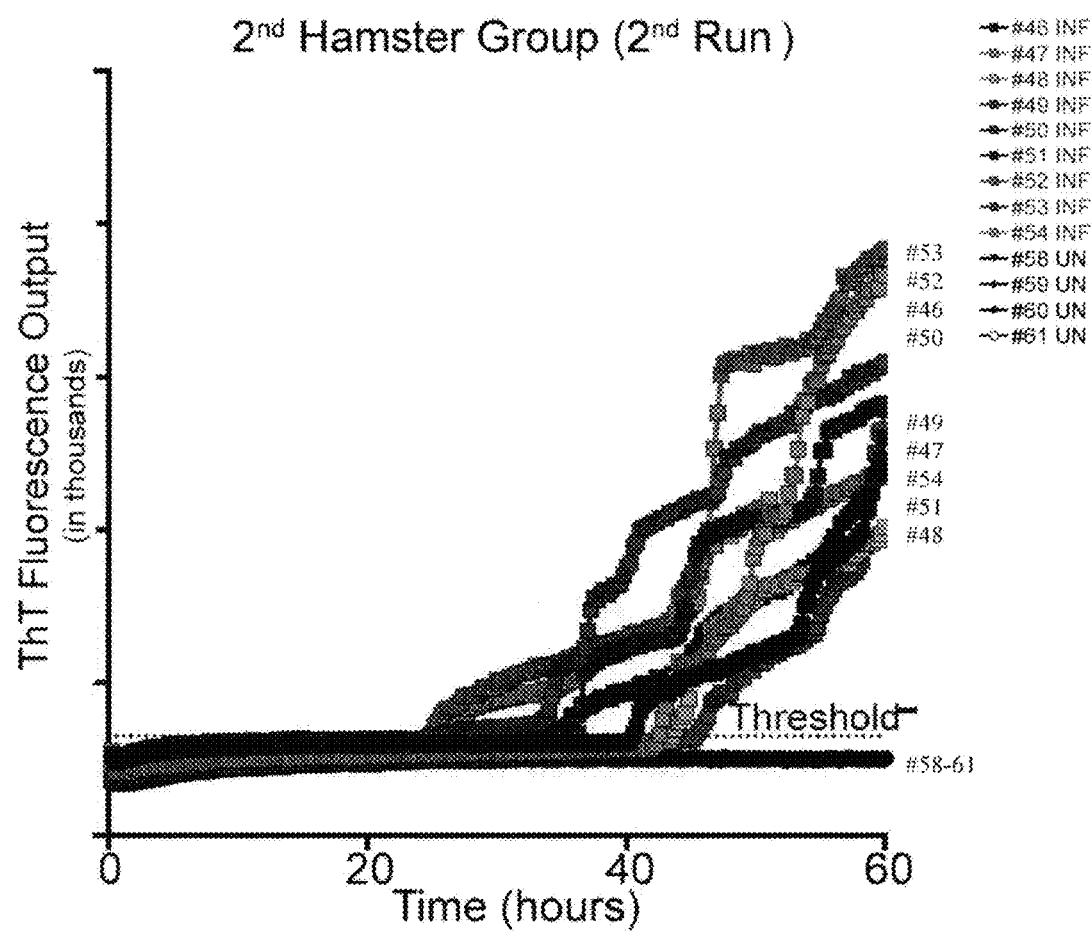

Example 6—Detection of Prion Converting Activity in TME-Infected Hamster Whole Blood The hyper strain of transmissible mink encephalopathy (HY TME) was chosen for the RT-QuIC assay to determine the assays ability for $PrP^D$ detection in various species and strains of TSEs. All HY TME-infected hamsters (n=21) ranging from 6 to 20 weeks post infection exhibited RT151 QuIC $PrP^C$ converting activity in 5/8-8/8 replicates within 60 hours, while all (n=7) of the age matched controls failed to seed RT-QuIC (FIGS. 6A-6C, Table 2). As above, sample replicates were averaged on each plate and a positive threshold was set at five times the standard deviation of the negative control average.

TABLE 2

Hamster blood donor inoculation, clinical status, and assay results

| Animal # | Inoculum | Route of Inoculation | Disease Status | Sample Collection Date | IHC Status | Positive QuIC Replicates |
|---|---|---|---|---|---|---|
| 34 | 10 μl 10% HY TME brain homogenate | Extranasal | Sub-clinical* | 8 WPI | ND | 8/8 |
| 35 | 10 μl 10% HY TME brain homogenate | Extranasal | Sub-clinical* | 8 WPI | ND | 8/8 |
| 36 | 10 μl 10% HY TME brain homogenate | Extranasal | Sub-clinical* | 8 WPI | ND | 5/8 |
| 37 | 10 μl 10% HY TME brain homogenate | Extranasal | Sub-clinical* | 10 WPI | ND | 8/8 |
| 38 | 10 μl 10% HY TME brain homogenate | Extranasal | Sub-clinical* | 10 WPI | ND | 5/8 |
| 39 | 10 μl 10% HY TME brain homogenate | Extranasal | Sub-clinical* | 10 WPI | ND | 8/8 |
| 40 | 10 μl 10% HY TME brain homogenate | Extranasal | Sub-clinical | 12 WPI | – | 8/8 |
| 41 | 10 μl 10% HY TME brain homogenate | Extranasal | Sub-clinical | 12 WPI | – | 8/8 |
| 42 | 10 μl 10% HY TME brain homogenate | Extranasal | Sub-clinical | 12 WPI | – | 8/8 |
| 43 | 10 μl 10% HY TME brain homogenate | Extranasal | Sub-clinical | 14 WPI | – | 8/8 |

TABLE 2-continued

Hamster blood donor inoculation, clinical status, and assay results

| Animal # | Inoculum | Route of Inoculation | Disease Status | Sample Collection Date | IHC Status | Positive QuIC Replicates |
|---|---|---|---|---|---|---|
| 44 | 10 µl 10% HY TME brain homogenate | Extranasal | Sub-clinical | 14 WPI | + | 8/8 |
| 45 | 10 µl 10% HY TME brain homogenate | Extranasal | Sub-clinical | 14 WPI | + | 8/8 |
| 46 | 10 µl 10% HY TME brain homogenate | Extranasal | Sub-clinical | 16 WPI | + | 8/8 |
| 47 | 10 µl 10% HY TME brain homogenate | Extranasal | Sub-clinical | 16 WPI | + | 7/8 |
| 48 | 10 µl 10% HY TME brain homogenate | Extranasal | Sub-clinical | 16 WPI | + | 8/8 |
| 49 | 10 µl 10% HY TME brain homogenate | Extranasal | Sub-clinical | 18 WPI | ND | 8/8 |
| 50 | 10 µl 10% HY TME brain homogenate | Extranasal | Sub-clinical | 18 WPI | ND | 7/8 |
| 51 | 10 µl 10% HY TME brain homogenate | Extranasal | Sub-clinical | 18 WPI | ND | 8/8 |
| 52 | 10 µl 10% HY TME brain homogenate | Extranasal | Clinical | 20 WPI | ND | 8/8 |
| 53 | 10 µl 10% HY TME brain homogenate | Extranasal | Clinical | 20 WPI | ND | 7/8 |
| 54 | 10 µl 10% HY TME brain homogenate | Extranasal | Clinical | 20 WPI | ND | 8/8 |
| 55 | 10 µl 10% sham homogenate | Extranasal | NA | 8 WPI | − | 0/8 |
| 56 | 10 µl 10% sham homogenate | Extranasal | NA | 10 WPI | − | 0/8 |
| 57 | 10 µl 10% sham homogenate | Extranasal | NA | 12 WPI | − | 0/8 |
| 58 | 10 µl 10% sham homogenate | Extranasal | NA | 14 WPI | − | 0/8 |
| 59 | 10 µl 10% sham homogenate | Extranasal | NA | 16 WPI | − | 0/8 |
| 60 | 10 µl 10% sham homogenate | Extranasal | NA | 18 WPI | − | 0/8 |
| 61 | 10 µl 10% sham homogenate | Extranasal | NA | 20 WPI | − | 0/8 |

WPI = weeks post inoculation
NA = Not available
ND = Not done
− = $PrP^D$ was not detected
+ = $PrP^D$ was detected in the sample
\* = Less than/equal to the halfway point to clinical disease Utilization of hamster models for the propagation and detection of hematogenous $PrP^D$ have been used extensively, primarily with scrapie infections. Previous to this study, RT-QuIC had not been used to probe for $PrP^C$ converting activity in whole blood of TME infected hamsters. To ensure that the detection of RT-QuIC blood-borne $PrP^D$ detection was not exclusive to CWD, we analyzed whole blood harvested from IHC-confirmed TME-infected and mock-infected hamsters. We have demonstrated $PrP^C$ converting activity in sub-clinical TME infected hamsters with 94.6% sensitivity and 100% specificity. We have also shown that the WBO RT-QuIC assay possesses the ability to detect $PrP^D$ in the blood of TME-infected hamsters prior to the mid point between inoculation and clinical disease.

These results reveal that RT-QuIC is consistently more sensitive in detection of hematogenous $PrP^D$ in sub-clinical animals than previously reported for PMCA Thus, the WBO RT-QuIC assay is applicable for the detection of prionemia in multiple species (animals/humans).

Example 7—Immunohistochemistry Confirmation of RT-QuIC Results

Figure 7:
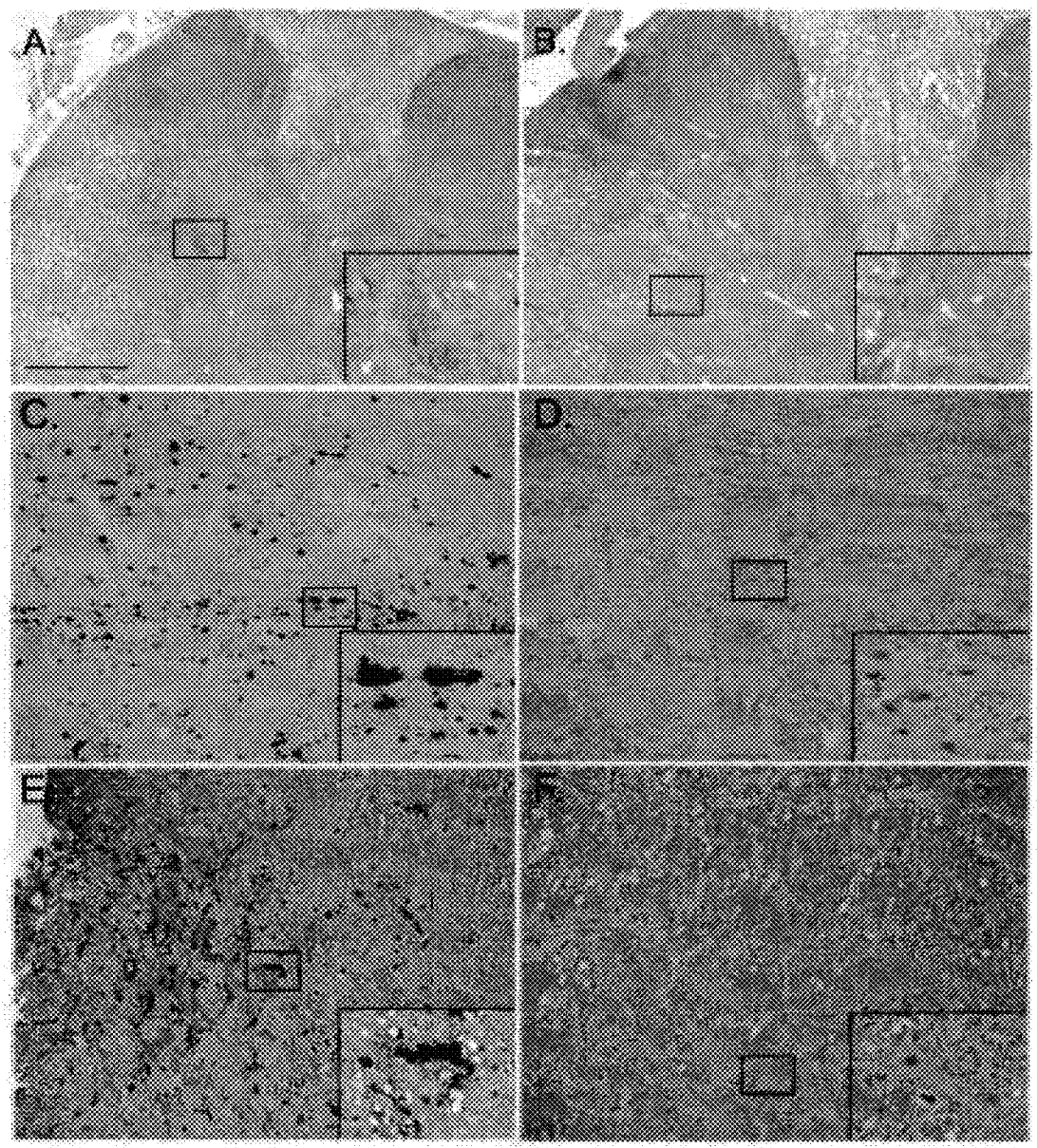
FIG. 7 is a series of six images (7A-7F) showing $PrP^D$ detection in hamster, white-tailed deer and muntjac by IHC. $PrP^D$ immunoreactivity in a spinal cord tissue section from a hamster 16 weeks after extranasal inoculation with HY-TME (A) detected with antibody 3F4 and ABC solution. $PrP^D$ immunoreactivity in the brainstem of CWD-infected white-tailed deer (C) and muntjac (E) detected with antibody BAR224 and AEC substrate. No immunoreactivity was seen in the corresponding tissues of mock-inoculated controls (B, D and E). The boxed areas are enlarged 10× in the insets. Scale bar=200 μm.

Immunohistochemistry was applied as a confirmation for the presence of $PrP^D$ deposition in animals where $PrP^C$ converting activity was detected in blood. IHC was performed on both cervid and hamster TME-inoculated and mock-inoculated brains for detection of the disease associated isoform of the prion protein, $PrP^D$. $PrP^D$ deposition was observed in TSE-infected animals, but not in mock-inoculated animals (FIG. 7; Tables 1, 2).

Example 8—Mouse and Hamster Bioassay Sensitivity vs. RT-QuIC Sensitivity

To determine the brain equivalent sensitivity of RT-QuIC for TME and CWD samples, RT-QuIC analysis of serial dilutions of TSE-positive brain homogenates were compared to lethal dose bioassay titrations in HY TME-infected hamsters and CWD-infected mice.

Figure 8A:
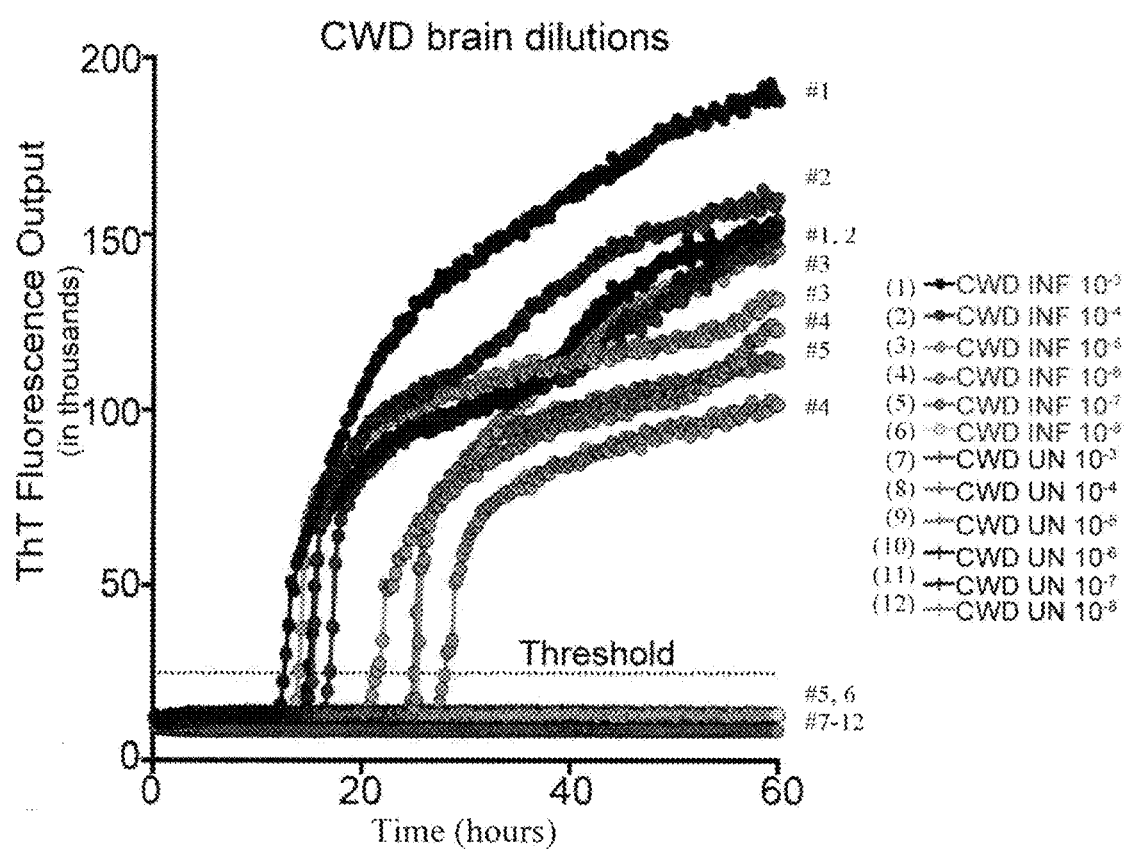
FIGS. 8A and 8B are a pair of graphs showing RT-QuIC analysis of serially diluted cervid and hamster brain samples. Brain samples were serially diluted $10^{-3}$ to $10^{-6}$ or $10^{-3}$ to $10^{-10}$ for cervids (A) and hamsters (B), respectively, and analyzed in RT-QuIC for 60 hours. A ThT fluorescence level above threshold determined positivity. Both cervid and hamster brains from positively inoculated animals demonstrated positivity in all dilutions, while all brain dilutions from naïve animals remained negative.
Figure 8B:
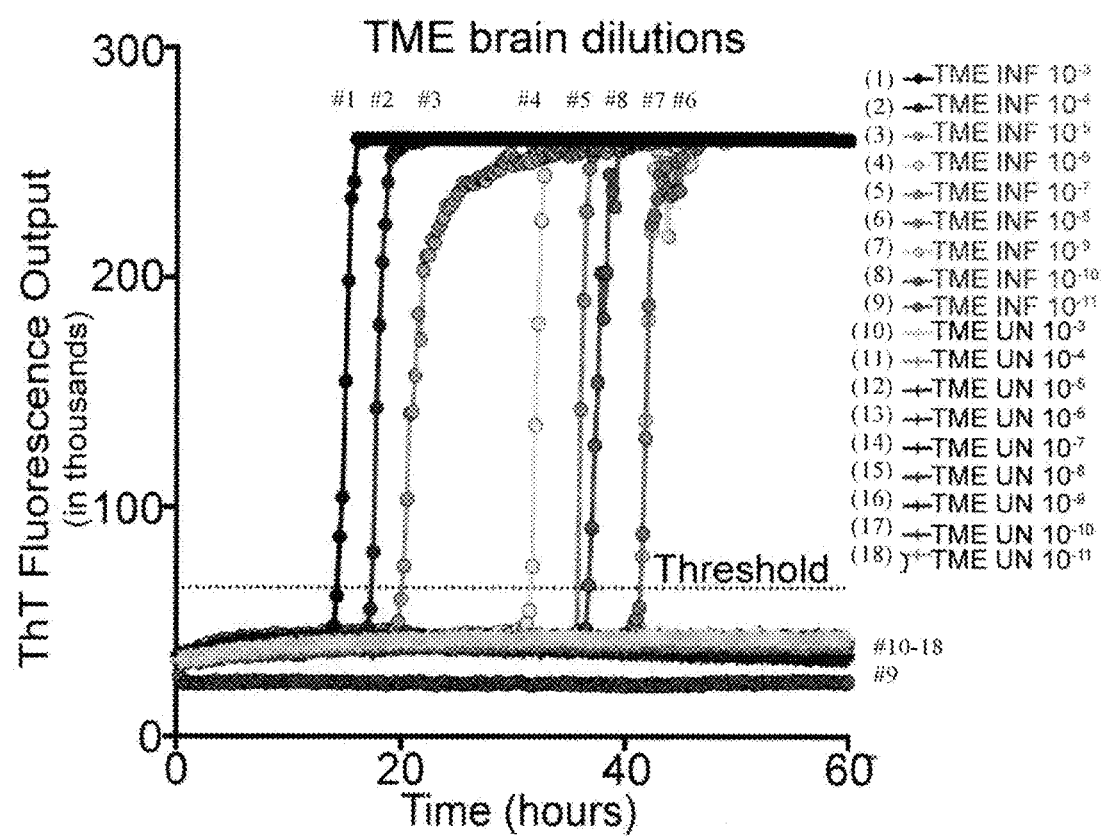

Using bioassay in cervidized transgenic mice, the LD50 titer for CWD-positive brain was determined to be a 0.001%, or $10^{-4}$, brain homogenate (Table 3). End point dilution analysis revealed a failure to cause disease in dilutions greater than $10^{-5}$. Serial dilutions of CWD-positive brain homogenates in RT-QuIC demonstrated consistent positivity to a dilution of $10^{-6}$ (FIG. 8A) indicating that the sensitivity of RT-QuIC for CWD detection is equal to or greater than animal bioassay.

TABLE 3

Bioassay of CWD-positive cervid brain in TgCerPrP mice

| Dose (% brain homogentate) | # Clinical/total n | Days post-inoculation (DPI) to clinical disease |
|---|---|---|
| 10 | 7/9[A] | 137 ± 63 DPI |
| 1 | 9/9 | 200 ± 29 DPI |

TABLE 3-continued

| Bioassay of CWD-positive cervid brain in TgCerPrP mice | | |
|---|---|---|
| Dose (% brain homogentate) | # Clinical/total n | Days post-inoculation (DPI) to clinical disease |
| 0.1 | 8/9[B] | 220 ± 70 DPI |
| 0.01 | 8/9[B] | 250 ± 68 DPI |
| 0.001 | 7/9 | 397 ± 152 DPI |
| 0.0001 | 1/9 | 335 DPI |
| 0.00001 | 0/9 | NA |

DPI = Days post inoculation

[A]= 2/9 mice died for reasons unrelated to CWD infection

[B]= 1/9 mice died for reasons unrelated to CWD infection

NA = Not applicable

The LD50 for hamsters intracranialy inoculated with HY TME was determined to be $10^{-8}$, as demonstrated previously by Kincaid, et al. [Kincaid, A. E. and J. C. Bartz, J Virol, 2007. 81(9): p. 4482-91.]. Endpoint dilution analysis resulted in failure to cause disease in dilutions greater than $10^{-9}$. RT-QuIC analysis of HY TME brain homogenates revealed $PrP^C$ converting activity to $10^{-10}$ (FIG. 8B) indicating that the sensitivity of RT-QuIC for HY TME detection is equal to or greater than animal bioassay.

Example 9—Materials and Methods

All animals were handled in strict accordance with guidelines for animal care and use provided by the United States Department of Agriculture (USDA), National Institutes of Health (NIH) and the Association for Assessment and Accreditation of Laboratory Animal Care International (AAALAC), and all animal work was approved by Colorado State University Institutional Animal Care and Use Committee (IACUC) Institutional Animal Care and Use Committee (IACUC) (approval numbers 02-151A, 08-175A and 11-2615A). All procedures involving hamsters were preapproved by the Creighton University Institutional Animal Care and Use Committee and were in compliance with the Guide for the Care and Use of Laboratory Animals.

Cervid Inoculation

Cervid whole blood was procured from historical and contemporary white-tailed and muntjac deer studies conducted at CSU (Table 1). In brief, naïve 1-2 year old white-tailed deer (*Odocoileus virginianus*) were inoculated with CWD-positive material as follows: 1) 1.0 g of brain in a 10% brain homogenate administered intracranialy [Mathiason, C. K., et al., Science, 2006. 314: p. 133-136.]; 2) 250 ml fresh/frozen whole blood administered intravenously/intraperitonealy, respectively; 3) 1.0 g of brain in a 10% brain homogenate administered orally; or 4) 2 ml of a 5% (wt/vol) brain homogenate aerosol-administered [Denkers, N. D., et al., J Virol, 2013. 87(3): p. 1890-2.]. Negative control white-tailed deer were exposed to sham inoculum as described above. Naïve 1-2 year old muntjac deer (Muntiacus reevesi) were inoculated with 1.0 g total brain in a 10% brain homogenate administered orally/subcutaneously [Nalls et al, PLoS One accepted; publication date pending]. Negative control muntjac deer received sham inoculum as described above.

Hamster Inoculation

Male 10-11 week old Syrian hamsters (Harlan Sprague Dawley, Indianapolis, Ind.) were used in these studies. Extranasal (e.n.) inoculations using a 10% w/v brain homogenate containing $10^{6.8}$ intracerebral 50% lethal doses per ml of the HY TME agent or a sham homogenate were performed as previously described [Kincaid, A. E., et al., J Virol, 2012. 86(23): p. 12731-40]. Hamsters receiving e.n. inoculations were briefly anesthetized with isoflurane (Webster Veterinary), placed in a supine position and 5 μl of brain homogenate was placed just inferior to each nostril (10 μl total volume). Brain homogenate was immediately inhaled into the nasal cavity, as hamsters are obligate nose breathers.

Blood and Tissue Collection from Cervids

Whole blood (10 ml/cervid/anticoagulant) was collected from n=22 CWD-inoculated cervids—six in various stages of disease presentation and 16 at termination—and from 11 negative control sham-inoculated cervids (Table 1). All blood samples were preserved in one of three anticoagulants: 1) 14% anticoagulant citrate phosphate dextrose adenine (CPDA), 2) 15% ethylenediaminetetraacetic acid (EDTA), or 3) 200 units/ml heparin, before being placed in 1 ml aliquots and frozen at −80° C. Brain (medulla oblongata) collected from each terminal white tailed deer and muntjac deer was frozen at −80° C. or fixed in 10% neutral buffered formalin or paraformaldehyde-lysine-periodate (PLP) and stored in 60% ethanol prior to processing.

Blood and Tissue Collection from Hamsters

At selected time points post-infection, three infected and one mock-infected hamsters were anesthetized with isoflurane and blood was collected via cardiac puncture into heparinized tubes for preservation at −80° C. (Table 2). The animals were then transcardially perfused with 50 ml of 0.01 M Dulbecco's phosphate buffered saline followed by 75 ml of McLean's PLP fixative. Brain and brainstem were immediately removed and placed in PLP for 5-7 hours at room temperature prior to paraffin processing and embedding.

Brain Tissue Homogenization

Ten percent (10%) brain tissue homogenates were created from the obex region of the medulla oblongata by homogenizing 0.5 g brain tissue in 0.5 ml homogenate buffer (1×PBS+0.1% Triton-X 100 [Sigma-Aldrich]). Samples were homogenized using 0.5 mm diameter zirconium oxide beads and a Bullet Blender (Next Advance) for 5 minutes at a speed setting of 10. Homogenates were stored at −80° C. in 20 μl aliquots.

Whole Blood Freeze-Thaw and Homogenization Process

One milliliter (1 ml) aliquots of whole blood were frozen at −80° C. for 30 minutes and subsequently thawed at 22° C. for 60 minutes. This process was repeated four times. Samples were then homogenized using 0.5 mm diameter zirconium oxide beads and a Bullet Blender (Next Advance) for 5 minutes at top speed.

Sodium Phosphotungstic Acid (NaPTA) Precipitation

Sodium phosphotungstic acid (NaPTA) precipitation of prions was used to concentrate proteins (including PrP) present in whole blood samples [D'Castro, L., et al., PLOS ONE, 2010. 5(12): p. e15679.]. Frozen whole blood homogenates were thawed and centrifuged at 2000 rpm for one minute to remove cellular debris. Five hundred microliters (500 μl) of supernatant was mixed with an equal volume of 4% sarkosyl in 1× phosphate buffered saline (PBS) and incubated for 30 minutes at 37° C. with constant agitation. Samples were then adjusted to contain a final concentration of 50 U/ml of benzonase (Sigma-Aldrich) and incubated at 37° C. for another 30 minutes with constant agitation. A solution of 4% (w/v) phosphotungstic acid (Sigma-Aldrich) and 170 mM magnesium chloride, adjusted to pH 7.4 with NaOH, was added to the sample for a final concentration of 0.3% (w/v) NaPTA and agitated at 37° C. for 30 minutes. Samples were then centrifuged for 30 minutes at 14,000 rpm and the pellet was resuspended in 50 μl 0.1% (v/v) sarkosyl.

Recombinant Protein Preparation

Recombinant protein was expressed and purified as previously described [Orru, C. D., et al., Protein Eng Des Sel, 2009. 22(8): p. 515-21]. Truncated recombinant Syrian hamster PrP (SHrPrP 90-231; received from the Caughey laboratory) expressed by Rosetta strain *Escherichia coli* was inoculated into 1 liter of LB containing Auto Induction™ supplements (EMD Biosciences). Cultures were allowed to grow overnight until harvest when an OD (600 nm) of ~3 was reached. Cells were lysed using Bug Buster™ and Lysonase™ (EMD Biosciences). Inclusion bodies (IB) were isolated by centrifugation at 15,000×g and were solubilized in 8M guanidine hydrochloride in Tris-phosphate buffer (100 mM $NaPO_4$ and 10 mM Tris pH 8.0). The protein solution obtained was bound to Super Flow Ni-NTA resin (Qiagen) pre-equilibrated with denaturing buffer (6.0 M GuHCl Tris-phosphate) at room temperature with agitation for 45 minutes and added to a XK FPLC column (GE). SHrPrP was refolded on the column with refolding Trisphosphate buffer at 0.75 ml/min for 340 ml, then eluted with 0.5 M imidazole Tris-phosphate pH 5.5 at 2.0 ml/min for a total of 100 ml. Eluted fractions were collected and dialyzed in two changes of 4.0 dialysis buffer (20 mM $NaPO_4$ pH 5.5). Following dialysis, purified protein was adjusted to 0.6 mg/ml, flash frozen in 1 ml aliquots, and stored at −80° C.

Real-Time Quaking Induced Conversion (RT-QuIC) Assay

Real-time quaking induced conversion (RT-QuIC), first described by Atarashi et al. [Atarashi, R., et al., Nat Methods, 2007. 4(8): p. 645-50], Wilham et al. [Wilham, J. M., et al., PLoS Pathog, 2010. 6(12): p. e1001217.], and Orru et al. [Orrú, C. D., et al., mBio, 2011. 2(3): p. e00078-11], was used for the conversion of small quantities of prions present in the blood of TSE-infected animals. Positive assay controls and samples consisted of serial dilutions of CWD/TME-infected brain ($10^{-3}$-$10^{-9}$) and blood ($10^{0}$-$10^{-6}$), respectively. Negative assay controls and samples were comprised of CWD/TME-naïve brain ($10^{-3}$-$10^{-9}$) and blood ($10^{0}$-$10^{-6}$), respectively. RT-QuIC reactions were set up in 96-well clear bottom optic plates (Nalgene Nunc) and consisted of 98 μl RT-QuIC Buffer (final concentrations of 1×PBS, 1 mM EDTA, 10 μM Thioflavin T (ThT), 100-200 mM NaCl buffer, and 0.1 mg/ml recombinant Syrian hamster $PrP^C$ substrate and 2 μl sample. Once reactions were set up in each well, plates were placed in a BMG Fluostar fluorescence plate reader with settings of 42° C. for 60 hours with cycles consisting of 1 minute shake, 1 minute rest and ThT fluorescence measurements were taken every 15 minutes. Data were removed from the fluorometer and processed using Microsoft Excel (Microsoft Inc.) prior to graph production with Prism 6 (GraphPad Prism).

Cervid Immunohistochemistry

Samples were processed and analyzed as previously described [Nalls et al, PLoS One accepted; publication date pending] In brief, fixed tissues were treated with formic acid, embedded in paraffin, cut and placed on positively charged slides. Deparaffinized, rehydrated and PK digested (20 mg/ml) tissues underwent epitope retrieval and were probed with primary antibody BAR224 (Cayman Chemical) and secondary anti-mouse HRP labeled polymer (Dako) prior to counterstain and reading by light microscopy Hamster Immunohistochemistry Immunohistochemistry was performed to detect $PrP^D$ as previously described [Kincaid, A. E., et al., J Virol, 2012. 86(23): p. 12731-40.]. In brief, deparaffinized, formic acid treated tissue sections were processed for antigen retrieval. Endogenous peroxidase and non-specific staining were blocked in $H_2O_2$ in methanol and normal horse serum. The sections were probed with monoclonal anti-PrP antibody 3F4 followed by secondary biotinylated horse anti-mouse immunoglobulin G conjugate prior to detection with ABC solution (Elite kit; Vector Laboratories). The sections were counterstained with hematoxylin and read by light microscopy Western Blotting Western blotting performed as previously described [Denkers, N. D., et al., J Virol, 2011. 85(3): p. 1396-9.62] with the following modifications: tissue homogenates were mixed with proteinase K (PK) (Invitrogen) to a final concentration of 50 μg/ml and incubated at 37° C. for 30 minutes, followed by incubation at 45° C. for 10 minutes with constant agitation. Samples were size fractionated on a NuPAGE 10% Bis-Tris gel (Novex) in 1×MOPS buffer at 100 volts for 2.5 hours, transferred to a polyvinylidene fluoride (PVDF) membrane for 7 minutes using the Trans-blot Turbo transfer system (Biorad). Post-transfer, the PVDF membrane was loaded onto a wetted SNAP i.d. holder (Millipore) and placed in the SNAP i.d. vacuum filtration system (Millipore). The PVDF membrane was blocked for 10 minutes with Blocking Buffer (Blocker casein in TBS [Thermo Scientific] with 0.1% Tween 20), and incubated for 10 minutes with 0.2 μg/ml primary antibody BAR224 (Cayman Chemical)—HRP conjugated antibody. The membrane was washed with TBST and developed using ECL Plus enhanced chemiluminescence Western blotting detection reagents (Invitrogen) and imaged on a Luminescence image analyzer LAS 3000 (Fujifilm).

Mouse Titration Bioassay

All animals were handled in strict accordance with guidelines for animal care and use provided by the United States Department of Agriculture (USDA), National Institutes of Health (NIH) and the Association for Assessment and Accreditation of Laboratory Animal Care International (AAALAC), and all animal work was approved by Colorado State University Institutional Animal Care and Use Committee (JACUC). Seven cohorts of TgCerPrP mice (n=9) were inoculated with 30 il of a CWD-infected cervid brain homogenate intracranialy. Each cohort received a different concentration of inoculum ranging from 10% (w/v) to 0.00001% (w/v). Negative control mice were inoculated with sham material. Mice were subsequently observed and terminated upon onset of clinical disease. All mice were analyzed for the presence of PrPD by Western blot and immunohistochemistry.

Glossary of Claim Terms

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "recombinant protein", or "recombinant PrP" refers to a protein/PrP encoded by a gene, a recombinant DNA, that has been cloned in a system that supports expression of the gene and translation of messenger RNA. Modification of the gene by recombinant DNA technology can lead to expression of a mutant protein. Proteins co-expressed in bacteria will not possess post-translational modifications, e.g. phosphorylation or glycosylation; eukaryotic expression systems are needed for proper post-translational modifications.

The term "recombinant DNA" refers to DNA sequences that result from the use of laboratory methods (molecular cloning) to bring together genetic material from multiple sources, creating sequences that would not otherwise be found in biological organisms.

The term "conformer" refers to a form of a compound having a particular molecular conformation. As used herein, the PrP protein can be folded as a non-pathogenic conformer (e.g. $PrP^C$, and $PrP^{sen}$) and a "mis-folded", pathogenic conformer (e.g. $PrP^D$, $PrP^{res}$, or $PrP^{Sc}$).

The term "conformational diseases" refers to that group of disorders arising from a propagation of an aberrant conformational transition of an underlying protein, leading to protein aggregation and tissue deposition. Such diseases can also be transmitted by an induced conformational change, propagated from a pathogenic conformer to its normal or non-pathogenic conformer and in this case they are called herein "transmissible conformational diseases". Examples of such kinds of diseases are the prion encephalopathies, including the bovine spongiform encephalopathy (BSE) and its human equivalent Creutzfeld-Jakob (CJD) disease, in which the underlying protein is the PrP.

The term "prion" shall mean a transmissible particle known to cause a group of such transmissible conformational diseases (spongiform encephalopathies) in humans and animals. The term "prion" is a contraction of the words "protein" and "infection" and the particles are comprised largely if not exclusively of $PrP^{Sc}$ molecules.

Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used and in particular in humans and in domesticated farm animals.

Protein Misfolding Cyclic Amplification, or "PMCA" is a technique that amplifies the prion disease-associated isoform of prion protein ($PrP^D$) in a sample by mixing the sample with an excess of the normal, non-pathogenic isoform of prion protein ($PrP^C$). The technique generally employs multiple rounds of amplification and disaggregation of the resulting product. More specifically, the starting $PrP^D$ in the sample, if any, converts the $PrP^C$ in the reaction mix to aggregates of the misfolded $PrP^D$ during the amplification phase of incubation. The resulting aggregates of $PrP^D$ are then dispersed, such as by sonication, to break up the aggregates into smaller chains. These smaller units of $PrP^D$ are then able to convert more of the $PrP^C$ in the sample into further aggregates of $PrP^D$. Brain homogenate from an uninfected animal is used as the source of the $PrP^C$.

Serial Protein Misfolding Cyclic Amplification, or "sPMCA", is a modification of the PMCA technique whereby additional, fresh $PrP^C$ is added to the reaction mix after a number of rounds of amplification to prime additional conversion and boost the amplification of the $PrP^D$ in the sample. Seeded PMCA replaced the brain homogenate as the source of the $PrP^C$ with a recombinant $PrP^{sen}$.

Quaking Induced Conversion, or "QuIC", is a further modification of prior $PrP^D$ amplification techniques, using shaking of the reaction mix instead of sonication. Quaking Induced Conversion in its standard form employed tube-based reactions mixes, with the subsequent immunoblotting detection of the resulting $PrP^{res}$ product.

Heparin is a naturally occurring mucopolysaccharide that acts in the body as an antithrombin factor to prevent intravascular clotting. The substance is produced by basophils and mast cells, which are found in large numbers in the connective tissue surrounding capillaries, particularly in the lungs and liver. In the form of sodium salt, heparin is used therapeutically and in blood collection procedures as an anticoagulant. Heparin acts primarily through a complex that it forms with antithrombin III. This complex accelerates the inhibition of thrombin and activated Factor X to prevent clotting or activation of thrombin, which in turn prevents the formation of fibrin from fibrinogen. The source of heparin is usually either bovine or porcine lungs and intestines. Samples can be collected in heparinized tubes or heparin can be added to a sample. Common concentrations are 2 units per mL, 10 units per mL, 50 units per mL, 100 units per mL, or 200 units per mL.

The phrase "an excess of a non-pathogenic conformer" of PrP, or a like phrase, refers to providing a sufficient amount of $PrP^C$ or rPrP such that a minute or undetectable level of $PrP^D$ in a sample can be amplified to detectable levels by having a sufficient quantity of the substrate $PrP^C$ or rPrP to achieve at least such detectable levels.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y.; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

Abbreviations used herein include:
CNS for central nervous system;
BSE for bovine spongiform encephalopathy;
CJD for Creutzfeldt-Jakob Disease;
CWD for chronic wasting disease (CWD);
CDPA for citrate phosphate dextrose adenine;
EDTA for ethylenediaminetetraacetic acid;
IHC for immunohistochemistry;
NaPTA for sodium phosphotungstic acid;
PMCA for protein misfolding cyclic amplification;
PrP for prion protein;
$PrP^C$ for the normal, non-pathogenic isoform of prion protein (PrP). This is sometimes referred to elsewhere as $PrP^{sen}$ as the prion protein is sensitive to protease digestion;
$PrP^D$ for the prion disease-associated isoform of prion protein (PrP). This is sometimes referred to elsewhere as $PrP^{res}$ as the prion protein is resistant to protease digestion or $PrP^{Sc}$ for the pathogenic or "scrapie" isoform of PrP;
$PrP^{Sc}$ for the pathogenic or "scrapie" isoform of PrP (which is also the marker for prion diseases);
QUIC for quaking-induced conversion assay;
rPrP for recombinant prion protein;
RT-QuIC for real-time quaking-induced conversion assay;
sPMCA for serial protein misfolding cyclic amplification;
ThT for thioflavin T;
TSE for transmissible spongiform encephalopathy;
vCJD for Variant Creutzfeldt-Jakob disease.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the amplification of a prion disease-associated conformer of prion protein ($PrP^D$) in a blood sample comprising the steps of:
   providing a blood sample containing a $PrP^D$;
   freezing the blood sample;
   thawing the blood sample;
   repeating the freezing and thawing steps one or more times;
   contacting the blood sample with an excess of a non-pathogenic conformer of $PrP^C$ or a non-pathogenic conformer of recombinant PrP;
   incubating the blood sample with the non-pathogenic conformer;
   disaggregating any aggregates of $PrP^D$ formed during the incubating step; and
   repeating the incubating and disaggregating steps one or more times to yield an amplified $PrP^D$ in the sample.

2. The method for the amplification of a prion disease-associated conformer of prion protein in a blood sample according to claim 1 wherein the steps of freezing and thawing are performed a plurality of times.

3. The method for the amplification of a prion disease-associated conformer of prion protein in a blood sample according to claim 1 wherein the steps of freezing and thawing are performed four or more times.

4. The method for the amplification of a prion disease-associated conformer of prion protein in a blood sample according to claim 1 wherein the samples are frozen to about −80° C. or colder.

5. The method for the amplification of a prion disease-associated conformer of prion protein in a blood sample according to claim 1 wherein the samples are frozen to about −20° C. or colder.

6. The method for the amplification of a prion disease-associated conformer of prion protein in a blood sample according to claim 1 wherein the samples are frozen at about −80° C. or colder for about 30 or more minutes.

7. The method for the amplification of a prion disease-associated conformer of prion protein in a blood sample according to claim 1 wherein the samples are thawed at about 22° C. or warmer.

8. The method for the amplification of a prion disease-associated conformer of prion protein in a blood sample according to claim 1 wherein the samples are thawed at about 4° C. or warmer.

9. The method for the amplification of a prion disease-associated conformer of prion protein in a blood sample according to claim 1 wherein the samples are thawed at about 22° C. or warmer for about 60 minutes.

10. The method for the amplification of a prion disease-associated conformer of prion protein in a blood sample according to claim 1 further comprising the step of precipitating the $PrP^D$ in a blood sample sodium phosphotungstic acid (NaPTA) following the thawing step and prior to amplifying the $PrP^D$.

11. The method for the amplification of a prion disease-associated conformer of prion protein in a blood sample according to claim 1 further comprising the step of screening the amplified $PrP^D$ for the presence of $PrP^D$.

12. The method for the amplification of a prion disease-associated conformer of prion protein in a blood sample according to claim 1 further comprising the steps of contacting the sample with thioflavin T (ThT) prior to an incubating step and measuring the fluorescence of the resulting sample after an incubating step, whereby the fluorescence of the ThT in the sample following incubation allows the presence of $PrP^D$ in the sample to be determined.

13. A method for the detection of a prion disease-associated conformer of prion protein ($PrP^D$) in a sample comprising the steps of:
providing a sample to be screened for $PrP^D$;
freezing and thawing the sample two (2) or more times;
contacting the thawed sample with an excess of a non-pathogenic conformer of $PrP^C$ or a non-pathogenic conformer of recombinant PrP;
incubating the contacted sample with the non-pathogenic conformer;
disaggregating any aggregates of $PrP^D$ formed during the incubating step;
repeating the incubating and disaggregating steps one or more times to yield an amplified $PrP^D$ in the sample; and
screening the incubated sample for $PrP^D$, whereby the method amplifies the $PrP^D$ in the sample to detectable levels.

14. The method for the amplification of a prion disease-associated conformer of prion protein in a blood sample according to claim 13 further comprising the steps of contacting the sample with ThT prior to an incubating step and measuring the fluorescence of the resulting sample after an incubating step, whereby the fluorescence of the ThT in the sample following incubation allows the presence of $PrP^D$ in the sample to be determined.

15. The method according to claim 13 wherein the samples are blood samples and the samples are frozen at about −20° C. or colder for about 30 minutes or more and subsequently thawed at about 4° C. or warmer for about 60 minutes or more.

16. The method according to claim 13 wherein the samples are subjected to at least four (4) freeze-thaw cycles.

17. The method according to claim 13 further comprising the step of homogenizing the sample after the freezing and thawing steps.

18. A method for the detection of a prion disease-associated conformer of prion protein ($PrP^D$) in a blood sample comprising the steps of:
providing a blood sample to be screened for $PrP^D$;
freezing and thawing the blood sample two (2) or more times;
contacting the blood sample with an excess of a non-pathogenic conformer of recombinant PrP;
incubating the blood sample with the non-pathogenic conformer;
disaggregating any aggregates of $PrP^D$ formed during the incubating step;
repeating the incubating and disaggregating steps one or more times to yield an amplified $PrP^D$ in the sample; and
screening the incubated sample for $PrP^D$, whereby the method amplifies the $PrP^D$ in the sample to detectable levels.

\* \* \* \*